United States Patent [19]

Sakakibara et al.

[11] Patent Number: 5,654,399

[45] Date of Patent: Aug. 5, 1997

[54] TETRAPEPTIDE DERIVATIVE HAVING ANTITUMOR ACTIVITY

[75] Inventors: Kyoichi Sakakibara, Tokyo; Masaaki Gondo, Yokohama; Koichi Miyazaki, Ebina, all of Japan

[73] Assignee: Teikoku Hormone Mfg. Co., Ltd., Tokyo, Japan

[21] Appl. No.: 498,688

[22] Filed: Jul. 3, 1995

Related U.S. Application Data

[62] Division of Ser. No. 190,194, filed as PCT/JP92/01005, Aug. 6, 1992.

[30] Foreign Application Priority Data

Aug. 9, 1991 [JP] Japan ................ 3-223534
Aug. 12, 1991 [JP] Japan ................ 3-225391

[51] Int. Cl.$^6$ ............... C07K 5/00; C07K 7/00; C07K 17/00; A61K 38/00
[52] U.S. Cl. .......................... 530/330
[58] Field of Search ................ 530/330; 514/18

[56] References Cited

U.S. PATENT DOCUMENTS

| | | | |
|---|---|---|---|
| 4,816,444 | 3/1989 | Pettit et al. | 514/17 |
| 4,978,744 | 12/1990 | Pettit et al. | 530/330 |
| 5,017,691 | 5/1991 | Lee et al. | 535/351 |

FOREIGN PATENT DOCUMENTS

| | | |
|---|---|---|
| 0 600 744 | 6/1994 | European Pat. Off. |
| 0 600 745 | 6/1994 | European Pat. Off. |
| 2-167278 | 6/1990 | Japan . |

OTHER PUBLICATIONS

Pettit et al., J. Am. Chem. Soc., "The Isolation and Structure of a Remarkable Marine Animal Antineoplastic Constituent: Dolastain 10$^{1a}$", vol. 109, pp. 6883–6885 (1987).
Schröder et al., The Peptides, vol. 1, "Formation of the Peptide Bond", pp. 76–136 (1965).
Bai et al., Biochemical Pharmacology, "Structure–Activity Studies with Chiral Isomers and with Segments of the Antimitotic Marine Peptide Dolastatin 10", vol. 40, No. 8, pp. 1859–1864 (1990).
Pettit et al., J. Med. Chem., "Chiral Modifications of Dolastatin 10: The Potent Cytostatic Peptide (19aR)–Isodolastatin 10$^1$", vol. 33, pp. 3132–3133 (1990).

Primary Examiner—Toni R. Scheiner
Assistant Examiner—Sheela J. Huff
Attorney, Agent, or Firm—Wenderoth, Lind & Ponack

[57] ABSTRACT

A tetrapeptide derivative represented by the following formula or a salt thereof has a higher cyto-static activity than dolastatin 10, and is useful as an antitumor agent:

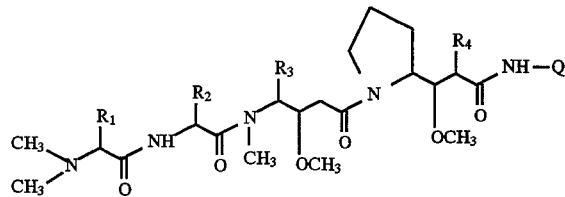

wherein, $R_1$, $R_2$, $R_3$ and $R_4$ are the same or different and each represent a hydrogen atom, a lower alkyl group or an aralkyl group;

Q represents

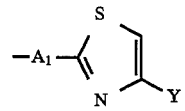

or a group of —$A_2$—$R_7$, wherein, $A_1$ represents a direct bond or

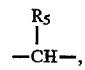

Y represents a hydrogen atom or —$COR_6$, $R_5$ represents a hydrogen atom, a lower alkyl group or an aralkyl group, $R_6$ represents a hydroxyl group, a lower alkoxy group, an aralkyloxy group or

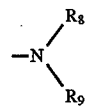

wherein, $R_8$ and $R_9$ are the same or different and each represent a hydrogen atom, a lower alkyl group, a phenyl group or a 4- to 7-membered heterocyclic group containing one or two hetero atoms selected from S, O and N, or alternatively $R_8$ and $R_9$ may combine together with the nitrogen atom to which they are bonded to form a 4- to 7-membered heterocyclic ring optionally further containing one hetero atom selected from S, O and N, $A_2$ represents a direct bond or a lower alkylene group, and $R_7$ represents a cycloalkyl group, an aryl group or an indolyl group, provided that the case is excluded where both $R_1$ and $R_2$ represent isopropyl groups, $R_3$ represents a sec-butyl group, $R_4$ represents a methyl group, and Q represents an α-(2-thiazolyl)phenethyl group.

4 Claims, No Drawings

TETRAPEPTIDE DERIVATIVE HAVING ANTITUMOR ACTIVITY

This application is a division of application Ser. No. 08/190,194, filed Feb. 9, 1994, which application is a U.S. National Phase application of International Application No. PCT/JP92/01005, filed Aug. 6, 1992.

BACKGROUND OF THE INVENTION

1. Field of the Invention

This invention relates to a novel tetrapeptide derivative having an antitumor activity, and relates more particularly to a tetrapeptide derivative represented by the following formula or a salt thereof:

(I)

[Chemical structure of formula (I)]

wherein, $R_1$, $R_2$, $R_3$ and $R_4$ are the same or different and each represent a hydrogen atom, a lower alkyl group or an aralkyl group;

Q represents

[Chemical structure showing —A₁—thiazole with Y substituent]

or a group of —$A_2$—$R_7$, wherein, $A_1$ represents a direct bond or $$-\underset{\underset{R_5}{|}}{CH}-,$$

Y represents a hydrogen atom or —$COR_6$, $R_5$ represents a hydrogen atom, a lower alkyl group or an aralkyl group, $R_6$ represents a hydroxyl group, a lower alkoxy group, an aralkyloxy group or $$-N\underset{R_9}{\overset{R_8}{\diagdown}}$$

wherein, $R_8$ and $R_9$ are the same or different and each represent a hydrogen atom, a lower alkyl group, a phenyl group or a 4- to 7-membered heterocyclic group containing one or two hetero atoms selected from S, O and N, or alternatively $R_8$ and $R_9$ may combine together with the nitrogen atom to which they are bonded to form a 4- to 7-membered heterocyclic ring optionally further containing one hetero atom selected from S, O and N, $A_2$ represents a direct bond or a lower alkylene group, and $R_7$ represents a cycloalkyl group, an aryl group or an indolyl group, provided that the case is excluded where both $R_1$ and $R_2$ represent isopropyl groups, $R_3$ represents a sec-butyl group, $R_4$ represents a methyl group, and Q represents an α-(2-thiazolyl)phenethyl group.

2. Description of Related Art

Peptides having a cytostatic activity and/or an antineoplasm activity have been isolated from marine molluscs, sea hare *Dolabella auricularia* and these peptides are called dolastatins 1 to 15. Among them, dolastatin 10 is a pentapeptide extracted from *Dolabella auricularia* from the Indian Ocean in 1987 by G. R. Pettit, et al. and having the following structural formula, and is said to be the strongest cytostatic substance presently known (see G. R. Pettit, et al., J. Am. Chem. Soc., 109, 6883 (1987) and Japanese Laid-Open Patent Publication No. 167278/1992).

[Chemical structure of Dolastatin 10]

Dolastatin 10

Further, recently, publication was made on the total synthesis of dolastatin 10 itself (see, U.S. Pat. No. 4,978,744), but its derivatives have not so far been known at all.

The present inventors have intensely studied derivatives of dolastatin 10, and as a result they found that certain dolastatin analogs represented by the above formula (I) have a higher cytostatic activity than dolastatin 10. They further found that many of these compounds have a larger therapeutic ratio (maximum effective dose/dose at 30% prolongation of life) and a lower toxicity than dolastatin 10, and are thus excellent as an antitumor agent.

Namely, they found not only that amino acid analogs of dolastatin 10 exhibit a higher activity than the native dolastatin 10, but that the activity is, unexpectedly, extremely increased by introducing a carboxyl derivative into the thiazole ring. Further, they found, thoroughly astoundingly, that derivatives wherein the thiazole ring is eliminated show extremely higher activity than dolastatin 10.

SUMMARY OF THE INVENTION

The embodiments of this invention completed based on these findings can be classified into the following three categories.

(1) Amino acid-substituted compounds of dolastatin 10 and synthesis thereof (2) Carboxyl derivatives of the thiazole ring and synthesis thereof (3) Tetrapeptide derivatives wherein the thiazole ring is eliminatd and synthesis thereof The synthesis method of compounds belonging to category (1) is described in the later-shown Flow sheets 1, 2 and 3, and the synthesis method of compounds belonging to category (2) is described in the later-shown Flow sheets 4 and 5. Further, the synthesis method of compounds belonging to category (3) is described in the later-shown Flow sheet 6.

In the present description, the term "lower" means that the number of the carbon atoms of a group or compound to which this term is attached is 6 or less, preferably 4 or less.

In the above formula (I), the "lower alkyl group" may be either of straight-chain and branched-chain, and there can, for example, be mentioned a methyl, ethyl, n-propyl, isopropyl, n-butyl, isobutyl, sec-butyl, tert-butyl, isopentyl, neopentyl or isohexyl group, or the like and the "aralkyl group" means an aryl-lower alkyl group, and there can, for example, be mentioned a benzyl or phenethyl group, or the like. Further, the "lower alkoxy group" means a lower alkyl-O-group wherein the lower alkyl part has the above meaning, an there can, for example, be mentioned a methoxy, ethoxy, n-propoxy, isopropoxy or tert-butoxy group, or the like, and the "aralkyloxy group" means an aralkyl-O-group wherein the aralkyl part has the above meaning, and there can, for example, be mentioned a benzyloxy or phenethyloxy group, or the like. Further, the "lower alkylene group" may be either of straight-chain and branched-chain, and there can, for example, be mentioned a methylene, ethylene, trimethylene, tetramethylene, methylmethylene, propylene, ethylethylene or 1,2-dimethylethylene group, or the like, and as the "cycloalkyl group", there can be mentioned a cycloalkyl group having 3 to 7 carbon atoms such as, for example, a cyclopropyl, cyclopentyl, cyclohexyl or cycloheptyl group, and as the "aryl group" there can for example, be mentioned a phenyl or naphthyl group, or the like.

When $R_8$ and $R_9$ represents "a 4- to 7-membered heterocyclic group containing one or two hereto atoms selected from S, O and N", as examples of the heterocyclic group, there can be mentioned azetidinyl, furyl, thienyl, pyridyl, piperidinyl, azepinyl, thiazolyl, imidazolyl, oxazolyl, pyrimidinyl and pyridazinyl groups, etc. Further, when $R_8$ and $R_9$ "combine together with the nitrogen atom to which they are bonded to form a 4- to 7-membered heterocyclic ring optionally further containing one hetero atom selected from S, O and N", as examples of the heterocyclic ring, there can be mentioned azetidino, pyrrolidino, piperidino, 1-perhydroazepinyl, piperazino, morpholino and thiomorpholino groups, etc.

Thus, as examples of the group of

there can be mentioned amino, methylamino, ethylamino, tsopropylamino, tert-butylamino, dimethylamino, diethylamino, phenylamino, N-methyl-N-phenylamino, furylamino, pyridylamino, 2-thiazolylamino, imidazolylamino, pyrimidinylamino, pyrrolidino, piperidino and morpholino group, etc.

A group of compounds preferred among the compounds of the above formula (I) are compounds wherein Q represents

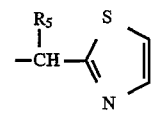

wherein $R_5$ has the same meaning as defined above, and particularly preferable among them are compounds wherein four groups among $R_1$, $R_2$, $R_3$, $R_4$, and $R_5$ represent the same groups as in dolastatin 10 (i.e., compounds wherein both $R_1$ and $R_2$ are isopropyl groups, $R_3$ is a sec-butyl group, $R_4$ is a methyl group and $R_5$ is a benzyl group), and only the residual one group represents a group different from that in dolastatin 10.

Another group of preferred compounds are the compounds of the case where $R_1$ and $R_2$ represent isopropyl groups, $R_3$ represents a sec-butyl group, $R_4$ represents a methyl group and Q represents

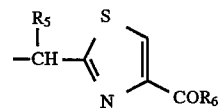

wherein
$R_5$ represents a benzyl group and $R_6$ has the same meaning as defined above.

Further, another group of preferred compounds are compounds of the case where Q represents —$A_2$—$R_7$ wherein $A_2$-represents a lower alkylene group and $R_7$ has the same meaning as defined above, and particularly preferable among them are compounds wherein both $R_1$ and $R_2$ represent isopropyl groups, $R_3$ represents a sec-butyl group, $R_4$ represents a methyl group and $R_7$ represents an aryl group.

In the compounds of the aforesaid formula (I) of this invention, the carbon atoms to which the substituents $R_1$, $R_2$, $R_3$, $R_4$, $R_5$ and methoxy groups are bonded are asymmetric carbon atoms, and can take arbitrary R or S configurations, and all these are included in the scope of this invention, but in view of the point of pharmacological activities, compounds which have the same configuration as dolastatin 10 are preferable.

DETAILED DESCRIPTION OF THE INVENTION

As representative examples of the compounds of the above formula (I) provided by this invention, there can be mentioned the following ones besides those mentioned in the later-described Examples.

| Compound No. | R₁ | R₂ | R₃ | R₄ | Q |
|---|---|---|---|---|---|
| 1 | i-Pr | i-Pr | i-Bu | Me | (thiazole)-CH= |
| 2 | Et | " | s-Bu | " | —CH(Bzl)-(thiazole) |
| 3 | n-Pr | " | " | " | " |
| 4 | i-Bu | " | " | " | " |
| 5 | i-Pr | n-Pr | " | " | " |
| 6 | " | i-Bu | " | " | " |
| 7 | " | i-Pr | H | " | " |
| 8 | " | " | Et | " | " |
| 9 | " | " | t-Bu | " | " |
| 10 | " | " | 1-Me-Bu | " | " |
| 11 | " | " | i-Pe | " | " |
| 12 | " | " | Bzl | " | " |
| 13 | " | " | s-Bu | Et | " |
| 14 | " | " | " | n-Pr | " |
| 15 | " | " | " | Me | —CH₂-(thiazole) |
| 16 | " | " | " | " | —CH(i-Pr)-(thiazole) |
| 17 | " | " | " | " | (thiazole)-COOCH₃ |
| 18 | " | " | " | " | (thiazole)-CONHEt |
| 19 | " | " | " | " | —CH(Bzl)-(thiazole)-COOH |
| 20 | " | " | " | " | —CH(Bzl)-(thiazole)-COOEt |
| 21 | " | " | " | " | —CH(Bzl)-(thiazole)-CONHMe |
| 22 | " | " | " | " | —CH(Bzl)-(thiazole)-CON(Et)₂ |

-continued

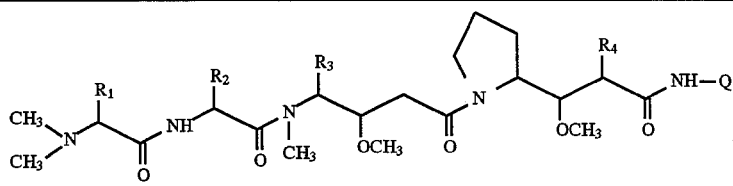

| Compound No. | R₁ | R₂ | R₃ | R₄ | Q |
|---|---|---|---|---|---|
| 23 | " | " | " | " | ![structure]  —CH(Bzl)— thiazole —CON(Me)(Ph) |
| 24 | " | " | " | " | —CH(Bzl)— thiazole —CONH-pyrimidine |
| 25 | " | " | " | " | —CH(Bzl)— thiazole —CON(piperidine) |
| 26 | " | " | " | " | —C₆H₁₁ (cyclohexyl) |
| 27 | " | " | " | " | -Np |
| 28 | " | " | " | " | —CH₂—C₆H₁₁ |
| 29 | " | " | " | " | —CH(Me)CH₂-Ph |
| 30 | " | " | " | " | —(CH₂)₄-Ph |
| 31 | " | s-Bu | " | " | —CH₂CH₂Ph |
| 32 | " | i-Pr | i-Pr | " | " |
| 33 | " | " | n-Pr | " | " |
| 34 | " | " | s-Bu | H | " |
| 35 | " | " | " | Et | " |

In the above groups, Me, Et, Pr, Bu, Pe, Bzl, Ph and Np mean a methyl group, an ethyl group, a propyl group, a butyl group, a pentyl group, a benzyl group, a phenyl group and a naphthyl group, respectively.

The tetrapeptide derivatives of the above formula (I) can exist as a salt, and examples of such salts, there can be mentioned hydrochlorides, hydrobromides, trifuloroacetates, p-toluenesulfonates and acetates.

According to this invention, a tetrapeptide derivative of the above formula (I) can be prepared by condensing amino acid or peptide fragments, for example according to the liquid phase synthesis method (see, E. Schröder and K. L übke, "The Peptides" volume 1 pages 76–136, 1965, published by Academic Press) well known in the field of peptide chemistry. However, it is most preferable to synthesize these tetrapeptide derivatives by condensing a tripeptide fragment of the following formula (II)

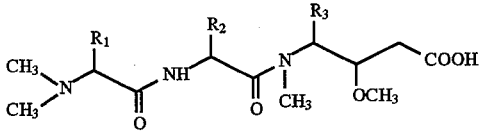

(II)

wherein R₁, R₂ and R₃ have the same meanings as defined above, with a fragment of the following formula (III)

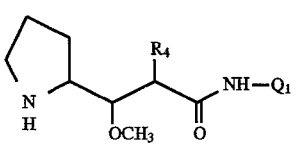

(III)

wherein R₄ has the same meaning as defined above, $Q_1$ represents a group of

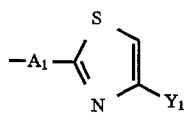

or

—$A_2$—$R_7$ wherein $Y_1$ represents a hydrogen atom or a methoxycarbonyl group, and $A_1$, $A_2$ and $R_7$ have the same meanings as defined above, because each fragments of the formulae (II) and (III) is easy to synthesize and is free from racemization at their condensation step. A compound in the case where, in the group Q, the substituent Y at the 4-position of the thiazole ring represents the group —$COR_6$ other than a methoxycarbonyl group, can be obtained by preparing a compound of the formula (I) wherein Y represents a methoxycarbonyl group and then converting the methoxycarbonyl group to a group —$COR_6$.

The reaction can generally be carried out by treating the above fragments (II) and (III) with a condensing agent, e.g. dicyclohexylcarbodiimide (DCC), diphenyl phosphoryl azide (DPPA) or diethyl phosphorocyanidate (DEPC), a so-called BOP reagent, or the like in an inert solvent such as, for example, chloroform, ethyl acetate, tetrahydrofuran (THF), dimethylformamide (DMF) or acetonitrile, if necessary in the presence of an organic base such as, for example, triethylamine, N-methylmorpholine or diisopropylethylamine (DIEA).

The reaction temperature is usually $-10°$ C. to room temperature, preferably around $0°$ C., and as for use rates of the compound of the formula (III), the organic base and the condensing agent based on the compound of the formula (II), it is advantageous to use the compound of the formula (III) of at least one mole, preferably of the order of 1.0 to 1.1 moles, the organic base of the order of 2 moles, and the condensing agent of the equimolar order, respectively per mole of the compound of the formula (II).

The conversion of a compound wherein the substituent Y at the 4-position of the thiazole ring in the group Q represents a methoxycarbonyl group to a compound wherein the substituent Y represents a group —CO—$R_6$ can easily be carried out, for example, when $R_6$ represents a hydroxyl group, by hydrolyzing the former compound with an alkali; when $R_6$ represents a lower alkoxy group or aralkyloxy group, by esterifying a compound wherein $R_6$ represents a hydroxyl group according to a conventional method; and when $R_6$ represents

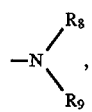

by treating the compound wherein the substituent Y represents a methoxycarbonyl group with ammonia, a primary amine or a secondary amine.

Thus, the desired tetrapeptide derivatives of the formula (I) are formed, and the isolation and purification thereof from the reaction mixtures can be carried out by recrystallization, ion exchange chromatography, gel filtration, high performance liquid chromatography, etc.

The compounds of the above formulae (II) and (III) used as starting materials in the above reaction are novel compounds not disclosed in prior literatures, and can easily be prepared by condensing amino acids, which are constituents thereof, according to a liquid phase synthesis method.

The tetrapeptide derivatives of the formula (I) of this invention have a higher cytostatic activity than dolastatin 10, and are useful for treatment of acute myelocytic leukemia, acute lymphocytic leukemia, chronic melanoma, pulmonary adenocarcinoma, neuroblastoma, pulmonary small cell carcinoma, breast cancer, colon cancer, ovary cancer, bladder cancer, etc.

The screening of cytostatic activity was made using lymphocytic leukemia P388 cells. The results are shown in the following Table.

TABLE

| Example No. of Compound | $ED_{50}$ (µg/ml) |
| --- | --- |
| 1 | $3.1 \times 10^{-6}$ |
| 4 | $1.7 \times 10^{-6}$ |
| 5 | $3.1 \times 10^{-5}$ |
| 15 | $2.4 \times 10^{-7}$ |
| 16 | $2.7 \times 10^{-5}$ |
| 23 | $<1.0 \times 10^{-6}$ |
| 25 | $<1.0 \times 10^{-6}$ |
| 26 | $<1.0 \times 10^{-6}$ |
| 28 | $2.9 \times 10^{-6}$ |
| Dolastatin 10 | $7.0 \times 10^{-4}$ |

The compounds of this invention, when used as a drug, can be used by formulating them into any dosage form of solid forms (e.g., tablets, hard capsules, soft capsules, granules, powders, fine granules, pills, troches, etc.), semi-solid forms (e.g., suppositories, ointments, etc.) and liquid forms (e.g., injections, emulsions, suspensions, lotions, sprays, etc.). As nontoxic additives usable in the above formulations, there can, for example, be mentioned starches, gelatin, glucose, lactose, fructose, maltose, magnesium carbonate, talc, magnesium stearate, methylcellulose, carboxymethyl-cellulose or salts thereof, gum arabic, polyethylene glycol, p-hydroxybenzoic acid alkyl esters, syrups, ethanol, propylene glycol, vaseline, carbowax, glycerol, sodium chloride, sodium sulfite, sodium phosphate, citric acid, etc. The drug can also contain another therapeutically effective drug.

The content of the compound of this invention in the drug varies depending on the dosage form, but it is generally preferable that the drug contains the compound at a concentration of 0.1 to 50 wt % in the case of solid and semi-solid forms, and at a concentration of 0.05 to 10 wt % in the case of liquid form.

The dose of the compound of this invention can widely be varied depending on the kind of warm-blooded animals including human beings who are subject, administration routes, the seriousness of symptoms, the diagnoses of doctors, etc., but can generally be on the order of 0.01 to 50 mg/kg per day. However, it is of course possible to administer the compound in an amount smaller than the lower limit of the above range or in an amount larger than the upper limit thereof in accordance with the seriousness of the symptom of the patient and the diagnosis of the doctor as mentioned above. The above dose can be administered once a day or divided into several portions per day.

This invention is further described below according to the Referential Examples and Examples.

As for the structure of compounds corresponding to compound numbers used in Referential Examples and Examples, please refer to the following Flow sheets 1 to 6. Therein, Z, Me, Bu$^t$, Boc and Bzl represent a benzyloxycarbonyl group, a methyl group, a tert-butyl group, a tert-butoxycarbonyl group and a benzyl group, respectively, and $R_1$, $R_2$, $R_3$, $R_4$, $R_5$, $R_6$ and —$A_2$—$R_7$ have the aforesaid meanings.

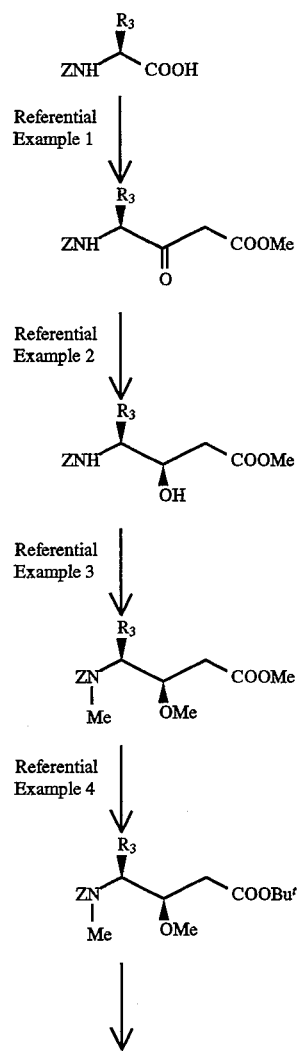

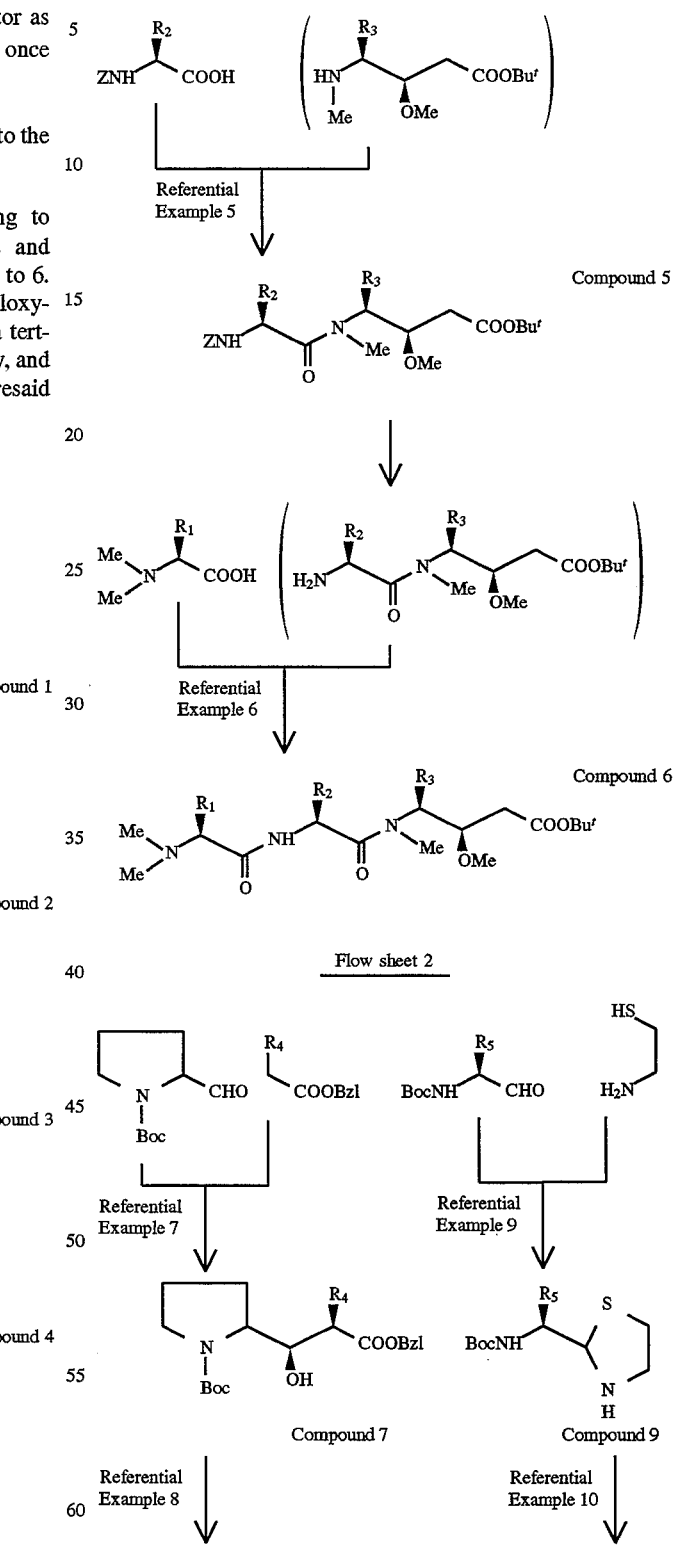

-continued
Flow sheet 2
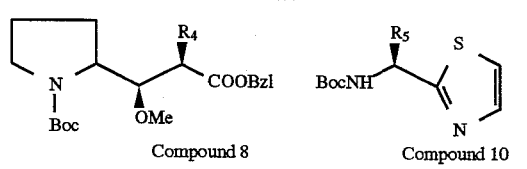
Compound 8    Compound 10
Reference Example 12
$(R_6 = OMe \longrightarrow OCH_2Ph)$
Flow sheet 4
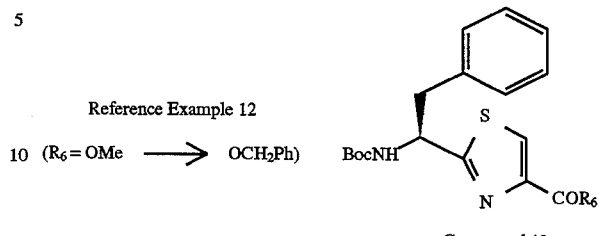
Compound 13
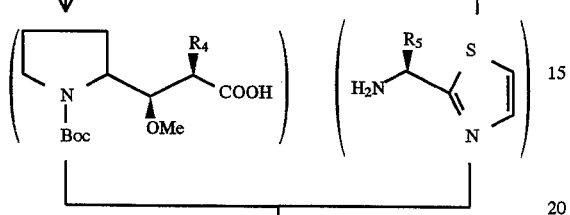
Referential Example 11
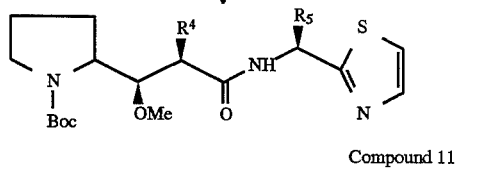
Compound 11
Flow sheet 3
Compound 6                Compound 11
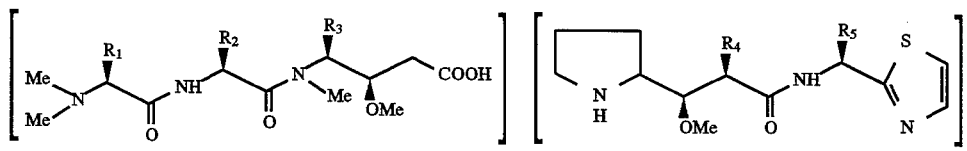
Examples 1 to 14
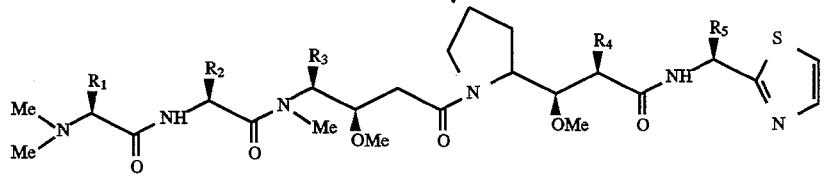
Compound 12

15
-continued
Flow sheet 4
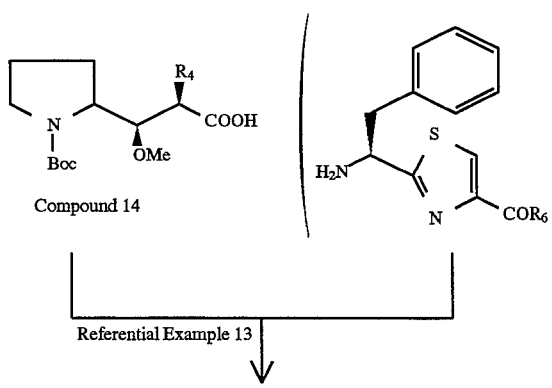
Compound 14
16
-continued
Flow sheet 4
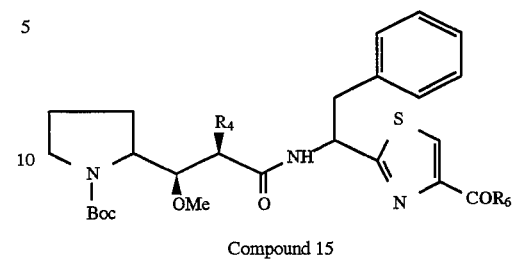
Compound 15
Referential Example 13
Flow Sheet 5
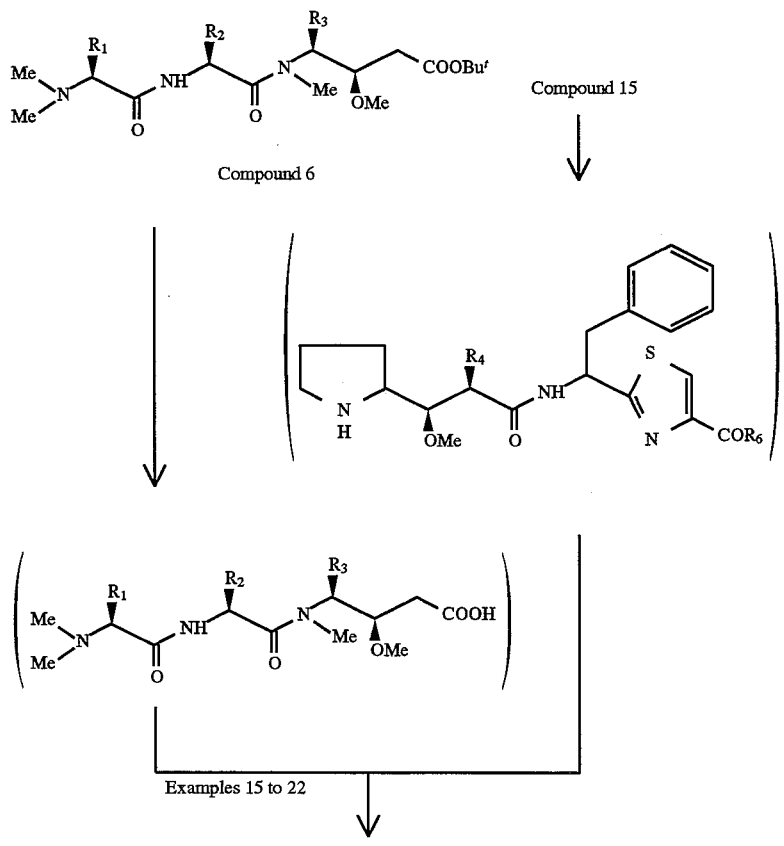
Examples 15 to 22

-continued
Flow Sheet 5
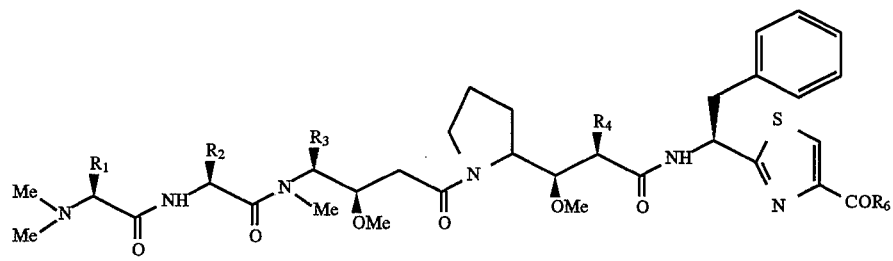
Compound 16
Flow Sheet 6
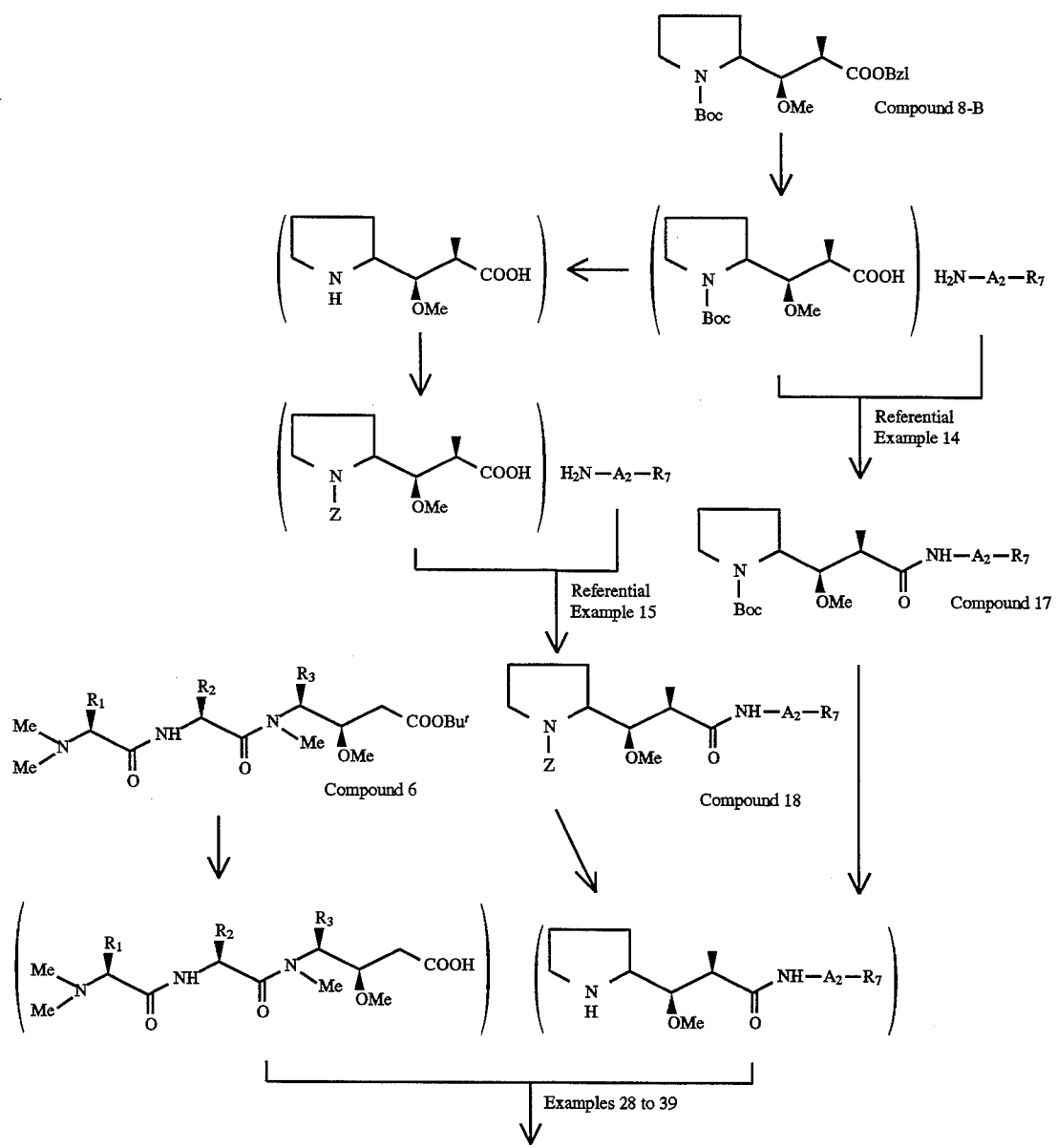

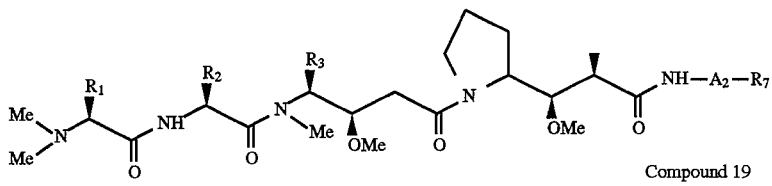

Compound 19

REFERENTIAL EXAMPLE 1-A

Preparation of compound 1-A (Compound 1 wherein $R_3=CH_3$)

11.15 g (50 mmoles) of Z-alanine is dissolved in 140 ml of tetrahydrofuran, 9.72 g (60 mmoles) of carbonyldiimidazole is added, and the mixture is stirred at room temperature for 4 to 5 hours.

On the other hand, 17.16 g (110 mmoles) of malonic acid monomethyl ester potassium salt and 7.60 g (80 mmoles) of anhydrous magnesium chloride are suspended in 150 ml of tetrahydrofuran and is stirred for 6 hours with heating on a water bath of 55°. The reaction mixture is cooled with ice, the above reaction solution is poured thereinto all at once, the cooling bath is immediately removed, and the mixture is stirred at room temperature for 24 to 48 hours.

A small amount of water is added to the reaction solution, and a clear supernatant is decanted from the deposited waxy precipitate, and concentrated under reduced pressure to obtain an oily matter. Ethyl acetate and ice-cooled 4N hydrochloric acid are added to each of the above waxy residue and this oily matter, each of the mixtures is shaken to dissolve, the two solutions are combined, the layers are separated, and the aqueous layer is extracted again with ethyl acetate. The ethyl acetate layer is washed with ice-cooled 2N hydrochloric acid and saturated aqueous sodium bicarbonate and dried, and the solvent is distilled off to obtain 13.50 g of a pale yellow oily matter. This is purified by silica gel column chromatography (eluent: ethyl acetate-n-hexane (1:1)) to obtain the desired compound 1-A as a colorless—pale yellow oily matter. 12.96 g (92.9%). $[\alpha]_D^{26} -17.7°$ (c=1.01 MeOH) $^1$H-NMR (CDCl$_3$, δ) 1.38(3 H, d, J=7.1 Hz), 3.55(2 H, s), 3.72(3 H, s), 4.45(1 H, m, J=7.1 Hz), 5.11(2 H, s), 5.25–5.55(1 H, m), 7. 34(5 H, s)

Referential Examples 1-B, 1-C, 1-D and 1-E were carried out in the same manner as in Referential Example 1-A to obtain compounds 1-B, 1-C, 1-D and 1-E as oily matters, respectively.

| Referential Example | Compound | R$_3$ | Yield | $[\alpha]_D$* | $^1$H-NMR (CDCl$_3$, δ) |
|---|---|---|---|---|---|
| 1-B | 1-B | CH$_3$CH$_2$CH$_2$— | 88.9% | N.D. | 0.75–1.05(6H, m), 1.1–2.1(4H, m), 3.54(2H, s), 3.72(3H, s), 4.1–4.6(1H, m), 5.11(2H, s), 5.2–5.5(1H, m), 7.34(5H, s) |
| 1-C | 1-C | CH$_3$\\CH—/CH$_3$ | 87.5% | −22.3° (26°) | 0.82(3H, d, J=6.8Hz), 1.03(3H, d, J=6.8Hz), 2.0–2.4(1H, m), 3.54(2H, s), 3.72(3H, s), 4.2–4.6(1H, m), 5.11(2H, s), 5.1–5.5 (1H, m), 7.34(5H, s) |
| 1-D | 1-D | CH$_3$\\CH—CH$_2$—/CH$_3$ | 93.7% | −35.2° (26°) | 0.8–1.05(6H, m), 1.1–1.9(3H, m), 3.55 (2H, s), 3.71(3H, s), 4.1–4.6(1H, m), 5.11(2H, s), 7.33(5H, s) |
| 1-E | 1-E | C$_2$H$_5$\\CH—/CH$_3$ | 99.2% | −27.6° (26°) | 0.6–1.5(9H, m), 3.54(2H, s), 3.71(3H, s), 4.2–4.5(1H, m), 5.10(2H, s), 5.15–5.45 (1H, m), 7.34(5H, s), |

*c = 1.00, MeOH

REFERENTIAL EXAMPLE 2-A

Preparation of compound 2-A (Compound 2 wherein $R_3=CH_3$)

12.96 g (46.45 mmoles) of compound 1-A obtained in Referential Example 1-A is dissolved in 380 ml of methanol, and 3.56 g (93.67 mmoles) of sodium borohydride is added thereinto all at once under stirring at −78°. Cooling and stirring are continued for 6 hours, ice-cooled 1N hydrochloric acid is added gradually, and when it is confirmed that the mixture becomes acidic, the mixture is concentrated under reduced pressure, and the deposited oily matter is extracted with ethyl acetate. The ethyl acetate layer is washed with saturated aqueous sodium bicarbonate and dried, and the solvent is distilled off to obtain 12.93 g of crystals. The crystals are recrystallized from isopropyl ether to obtain the desired compound 2-A as colorless needles of a melting point of 78°. 11.09 g (85.0%). $[\alpha]_D^{28} -4.4°$ (c=1.00, MeOH) As C$_{14}$H$_{19}$NO$_5$ Calculated C=59.77% H=6.81% N=4.98% Found C=59.83% H=6.92% N=5.07% $^1$H-NMR (CDCl$_3$, δ)

1.15(3 H, d, J=6.8 Hz), 2.35~2.55(2 H, m), 3.70(3 H, s), 3.85~4.15(1 H, m), 5.09(2 H, s), 7.34(5 H, s)

Referential Examples 2-B, 2-C, 2-D and 2-E were carried out in the same manner as in Referential Example 2-A to obtain compounds 2-B, 2-C, 2-D and 2-E, respectively.

under reduced pressure at 50° or below. The residue is thoroughly extracted with ethyl acetate, the ethyl acetate layer is washed with 5% sodium thiosulfate and saturated aqueous sodium bicarbonate and dried, and the solvent is distilled off to obtain 10.43 g of a yellow oily matter. The

| Referential Example | Compound | $R_3$ | Yield | Melting point | $[\alpha]_D$* | Analytical value | $^1$H-NMR (CDCl$_3$, δ) |
|---|---|---|---|---|---|---|---|
| 2-B | 2-B | $CH_3CH_2CH_2-$ | 88.1% | 126° | −13.6° (27°) | $C_{16}H_{23}NO_5$<br>☆ C 62.12%<br>H 7.49%<br>N 4.53%<br>★ C 61.99%<br>H 7.51%<br>N 4.75% | 0.75~1.05(3H, m), 1.1~1.7 (4H, m), 2.35~2.55(2H, m), 3.69(3H, s), 3.8~4.15 (1H, m), 4.65~4.95(1H, m), 5.10(2H, s), 7.34(5H, s) |
| 2-C | 2-C | $CH_3$<br>  \\<br>   CH—<br>  /<br>$CH_3$ | 80.7% | 81° | +9.6° (28°) | $C_{16}H_{23}NO_5$<br>☆C 62.12%<br>H 7.49%<br>N 4.53%<br>★C 62.16%<br>H 7.51%<br>N 4.70% | 0.87(3H, d, J=6.5Hz), 0.95 (3H, d, J=6.5Hz), 1.9~ 2.35(1H, m), 2.4~2.6 (2H, m), 3.18(1H, br, d), 3.69(3H, s), 4.45~4.80 (1H, m), 5.10 (2H, s), 7.34(5H, s) |
| 2-D | 2-D | $CH_3$<br>  \\<br>   CH—$CH_2$—<br>  /<br>$CH_3$ | 81.9% | 100° | −21.5° (26°) | $C_{17}H_{25}NO_5$<br>☆C 63.14%<br>H 7.79%<br>N 4.33%<br>★C 63.05%<br>H 7.76%<br>N 4.62% | 0.90(3H, d, J=6.2Hz), 0.92 (3H, d, J=6.2Hz), 1.1~1.8 (3H, m), 2.35~2.55(2H, dd), 3.69(3H, s), 3.8~4.15 (1H, m), 4.65~4.95(1H, m), 5.10(2H, s), 7.34(5H, s) |
| 2-E | 2-E | $C_2H_5$<br>  \\<br>   CH—<br>  /<br>$CH_3$ | 86.4% | 77° | +6.9° (27°) | $C_{17}H_{25}NO_5$<br>☆C 63.14%<br>H 7.79%<br>N 4.33%<br>★C 63.12%<br>H 7.78%<br>N 4.35% | 0.8~1.05(6H, m), 1.3~1.95 (3H, m), 2.4~2.6(2H, m), 3.1~3.25(1H, br, d), 3.69(3H, s), 3.8~4.15 (1H, m), 4.66(1H, br, d), 5.10(2H, s), 7.34(5H, s) |

*c = 1.00 MeOH
☆ Calculated
★ Found

REFERENTIAL EXAMPLE 3-A

Preparation of compound 3-A (Compound 3 wherein $R_3=CH_3$)

9.78 g (34.80 mmoles) of the compound obtained in Referential Example 2-A is dissolved in 100 ml of dimethylformamide, 40.0 g (172.41 mmoles) of silver oxide and 50 ml of methyl iodide are added, and the mixture is stirred for 5 hours in a water bath of 35°. The mixture is filtered, silver oxide is washed with dimethylformamide, and the filtrate and washings are combined and concentrated oily matter is purified by silica gel column chromatography (eluent: benzene-ethyl acetate (5:1)) to obtain the desired Compound 3-A as a pale yellow oily matter. 7.63 g (71.0%). $[\alpha]_D^{25}$−39.8° (c=1.03, MeOH) $^1$H-NMR (CDCl$_3$, δ) 1.21(3 H, d, J=6.8 Hz), 2.47(2 H, d, J=6.2 Hz), 2.80(3 H, s), 3.38(3 H, s), 3.64(3 H, s), 5.13(2 H, s), 7.34(5 H, s)

Referential Examples 3-B, 3-C., 3-D and 3-E were carried out in the same manner as in Referential Example 3-A to obtain compounds 3-B, 3-C, 3-D and 3-E as oily matters, respectively.

| Referential Example | Compound | $R_3$ | Yield | $[\alpha]_D$* | $^1$H-NMR (CDCl$_3$, δ) |
|---|---|---|---|---|---|
| 3-B | 3-B | $CH_3CH_2CH_2-$ | 72.5% | −50.7° (25°) | 0.75~1.05(3H, m), 1.05~1.8(4H, m), 2.48 (2H, t, J=5.5Hz), 2.75(3H, s), 3.36, 3.38 (3H, s), 3.63(3H, s), 5.13(2H, s), 7.34(5H, s) |
| 3-C | 3-C | $CH_3$<br>  \\<br>   CH—<br>  /<br>$CH_3$ | 67.9% | −20.7° (26°) | 0.8~1.15(6H, m), 1.8~2.2(1H, m), 2.4~2.6(2H, m), 2.80(3H, s), 3.31, 3.38 (3H, s), 3.65, 3.66(3H, s), 5.13(2H, s), 7.33(5H, s) |

-continued

| Referential Example | Compound | R₃ | Yield | [α]_D* | ¹H-NMR (CDCl₃, δ) |
|---|---|---|---|---|---|
| 3-D | 3-D | (CH₃)₂CH—CH₂— | 83.9% | −34.2° (26°) | 0.7~1.0(6H, m), 1.25~1.6(3H, m), 2.47 (2H, t, J=5.6Hz), 2.74(3H, s), 3.35, 3.37 (3H, s), 3.62(3H, s), 5.13(2H, s), 7.33(5H, s) |
| 3-E | 3-E | (C₂H₅)(CH₃)CH— | 74.4% | −4.0° (27°) | 0.7~1.1(6H, m), 1.1~1.9(3H, m), 2.4~2.6(2H, m), 2.78(3H, s), 3.29, 3.38 (3H, s), 3.66(3H, s), 3.75~4.2(2H, m), 5.13(2H, s), 7.33(5H, s) |

*c = 1.00, MeOH

REFERENTIAL EXAMPLE 4-A

Preparation of compound 4-A (Compound 4 wherein R₃=CH₃)

6.60 g (21.36 mmoles) of the compound 3-A obtained in Referential Example 3-A is dissolved in 100 ml of dioxane, 23.5 ml (23.5 mmoles) of 1N sodium hydroxide is added, and the mixture is stirred at room temperature for 2 to 3 hours. 20% citric acid is added to the reaction solution to make the pH 4.0, the mixture is concentrated under reduced pressure, and the deposited oily matter is extracted with ethyl acetate. The ethyl acetate layer is washed with saturated saline and dried, and the solvent is distilled off to give a colorless—pale yellow oily matter.

This is dissolved in 60 ml of dichloromethane, 0.8 ml of concentrated sulfuric acid is added, and the mixture is shaken with 25 ml of isobutene in a pressure bottle at room temperature for 48 to 96 hours. The reaction solution is poured into saturated aqueous sodium bicarbonate, nitrogen gas is blown thereinto to remove isobutene and the greater part of dichloromethane, the deposited oily matter is extracted with ethyl acetate, and the ethyl acetate layer is washed with saturated aqueous sodium bicarbonate land dried. The solvent is distilled off, and the remaining yellow oily matter (7.32 g) is purified by silica gel column chromatography (eluent: benzene-ethyl acetate (10:1)) to obtain 6.31 g (84.1%) of the desired compound 4-A as a colorless—pale yellow oily matter. [α]_D²⁷−33.0° (c=1.02, MeOH) ¹H-NMR (CDCl₃, δ) 1.21(3 H, d, J=6.8 Hz), 1.44(9 H, s), 2.38(2 H, d, J=6.2 Hz), 2.82(3 H, s), 3.38(3 H, s), 3.5~3.85(1 H, m), 3.85~4.4(1 H, m), 5.13(2 H, s), 7.34(5 H, s).

Referential Examples 4-B, 4-C, 4-D and 4-E were carried out in the same manner as in Referential Example 4-A to obtain compounds 4-B, 4-C, 4-D and 4-E as oily matters, respectively.

| Referential Example | Compound | R₃ | Yield | [α]_D* | ¹H-NMR (CDCl₃, δ) |
|---|---|---|---|---|---|
| 4-B | 4-B | CH₃CH₂CH₂— | 84.0% | −42.0° (27°) | 0.7~1.05(3H, m), 1.44(9H, s), 2.25~2.5 (2H, m), 2.77(3H, s), 3.37, 3.38(3H, s), 3.5~3.75(1H, m), 3.75~4.25(1H, m), 5.13(2H, s), 7.33(5H, s) |
| 4-C | 4-C | (CH₃)₂CH— | 75.2% | −17.8° (27°) | 0.8~1.1(6H, m), 1.45(9H, s), 1.75~2.25 (1H, m), 2.25~2.5(2H, m), 2.81(3H, s), 3.31, 3.39(3H, s), 3.7~4.05(2H, m), 5.13(2H, s), 7.33(5H, s) |
| 4-D | 4-D | (CH₃)₂CH—CH₂— | 75.8% | −28.9° (26°) | 0.7~1.0(6H, m), 1.44(9H, s), 2.25~2.5 (2H, m), 2.77(3H, s), 3.36(3H, s), 3.45~3.75(1H, m), 3.8~4.4(1H, m), 5.13(2H, s), 7.33(5H, s) |
| 4-E | 4-E | (C₂H₅)(CH₃)CH— | 87.6% | −12.0°** (27°) | 0.7~1.05(8H, m), 1.45(9H, s), 1.65~1.75 (1H, m), 2.3~2.45(2H, m), 2.79(3H, s), 3.29, 3.39(3H, s), 3.75~4.2(2H, m), 5.13(2H, s), 7.33(5H, s) |

*c = 1.00, MeOH
**CHCl₃

REFERENTIAL EXAMPLE 5-A

Preparation of compound 5-A (Compound 5 wherein $R_2 = (CH_3)_2CH-$, $R_3 = CH_3$)

0.70 g (2.00 mmoles) of compound 4-A obtained in Referential Example 4-A is dissolved in 20 ml of t-butanol-water (9:1), 0.1 g of 5% palladium carbon is added, and the mixture is stirred under a hydrogen stream for 2 hours. After the reaction, the catalyst is filtered and washed, and the filtrate and the washings are concentrated under reduced pressure. The remaining oily matter is dissolved in 30 ml of benzene, the solution is concentrated again under reduced pressure, and the operation is repeated once more. The resultant oily matter is dissolved together with 0.56 g (2.23 mmoles) of Z-valine in 10 ml of acetonitrile, and 0.43 g (2.09 mmoles) of DCC is added under ice cooling and stirring. Soon, crystals appear. Stirring is continued at 0° for at least 3 hours, and then overnight during which time the temperature is allowed to rise as the ice melts, the reaction mixture is diluted with ethyl acetate, and the crystals are filtered and washed with ethyl acetate. The filtrate and the washings are concentrated under reduced pressure, the syrupy residue is dissolved in ethyl acetate, the insoluble matters, if any, are removed by filtration, the ethyl acetate solution is washed with ice-cooled 2N hydrochloric acid and saturated aqueous sodium bicarbonate and dried, and the solvent is distilled off to obtain 1.01 g of a colorless oily matter. This is purified by silica gel column chromatography (eluent: benzene-ethyl acetate (5:1)) to obtain 0.67 g (74.4%) of the desired compound 5-A as a colorless oily matter. $[\alpha]_D^{28}$ −31.4° (c=1.02, MeOH) $^1$H-NMR (CDCl$_3$, δ) 0.8~1.1(6 H, m), 1.17(3 H, d, J=6.8 Hz), 1.45(9 H, s), 2.25~2.45(2 H, m), 3.00(3 H, s), 3.37(3 H, s), 3.68(1 H, dd, J=12.1 Hz, 6.2 Hz), 4.35~4.75(2 H, m), 5.09(2 H, s), 5.56 (1 H, br, d), 7.33(5 H, s)

The following compounds were obtained in the same manner as in Referential Example 5-A.

| Referential Example | Compound | R$_2$ | R$_3$ | Yield | [α]$_D$* | $^1$H-NMR (CDCl$_3$, δ) |
|---|---|---|---|---|---|---|
| 5-B | 5-B | (CH$_3$)$_2$CH— | CH$_3$CH$_2$CH$_2$— | 80.2% | −46.2° (27°) | 0.7~1.1(9H, m), 1.45(9H, s), 2.25~2.45(2H, m), 2.98(3H, s), 3.37(3H, s), 3.6~3.8(1H, m), 4.3~4.7(2H, m), 5.10(2H, s), 5.50(1H, br, d), 7.33(5H, s) |
| 5-C | 5-C | (CH$_3$)$_2$CH— | (CH$_3$)$_2$CH— | 73.6% | −32.9° (25°) | 0.75~1.1(12H, m), 1.46(9H, s), 2.25~2.45(2H, m), 2.97(3H, s), 3.35(3H, s), 3.7~4.0(1H, m), 4.3~4.7(2H, m), 5.09(2H, s), 5.48(1H, br, d), 7.32(5H, s) |
| 5-D | 5-D | (C$_2$H$_5$)(CH$_3$)CH— | (CH$_3$)$_2$CH— | 76.6% | −33.6° (25°) | 0.7~1.2(14H, m), 1.46(9H, s), 2.25~2.45(2H, m), 2.99(3H, s), 3.34(3H, s), 3.6~4.0(1H, m), 4.35~4.65(2H, dd, J=9.5Hz, 6.6Hz), 5.09(2H, s), 5.41(1H, br, d), 7.32(5H, s) |
| 5-E | 5-E | (CH$_3$)$_2$CH— | (CH$_3$)$_2$CH—CH$_2$— | 85.4% | −41.1° (27°) | 0.7~1.1(12H, m), 1.46(9H, s), 2.3~2.45(2H, m), 2.97(3H, s), 3.35(3H, s), 3.5~3.8(1H, m), 4.4~4.7(2H, m), 5.08(2H, s), 5.3~5.6(1H, br, d), 7.34(5H, s) |
| 5-F | 5-F | H | (C$_2$H$_5$)(CH$_3$)CH— | 58.7% | −11.0° (27°) | 0.7~1.1(6H, m), 1.45(9H, s), 2.3~2.45(2H, m), 2.82(3H, s), 3.36(3H, s), 3.75~4.15(3H, m), 5.12(2H, s), 5.8(1H, br), 7.34(5H, s) |
| 5-G | 5-G | (CH$_3$)$_2$CH— | (C$_2$H$_5$)(CH$_3$)CH— | 81.3% | −22.2° (26°) | 0.65~1.1(12H, m), 1.45(9H, s), 2.25~2.45(2H, m), 2.96(3H, s), 3.34(3H, s), 3.75~4.05(1H, m), 4.35~4.7(2H, m), 5.10(2H, s), 5.50(1H, br, d), 7.33(4H, s) |
| 5-H | 5-H | (C$_2$H$_5$)(CH$_3$)CH— | (C$_2$H$_5$)(CH$_3$)CH— | 62.6% | −26.5° (24°) | 0.17~1.1(12H, m), 1.45(9H, s), 2.25~2.45(2H, m), 2.97(3H, s), 3.34(3H, s), 3.7~4.05(1H, m), 4.35~4.7(2H, m), 5.09(2H, s), 5.43(1H, br, d), 7.32(5H, s) |
| 5-I | 5-I | PhCH$_2$— | (C$_2$H$_5$)(CH$_3$)CH— | 59.3% | −4.8° (26°) | 0.65~1.1(9H, m), 1.48(9H, s), 2.1~2.3(2H, m), 2.9~3.1(2H, m), 3.31(3H, s), 3.5~4.0(2H, m), 4.3~4.7(1H, m), 5.06(2H, s), 5.55(1H, br. d), 7.25(5H, s), 7.31(5H, s) |

*c = 1.00, MeOH

REFERENTIAL EXAMPLE 6-A

Preparation of compound 6-A (Compound 6 wherein

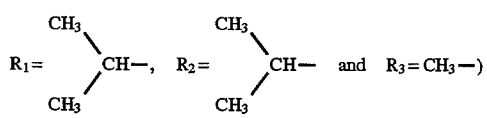

$R_1=$ (CH$_3$)$_2$CH—, $R_2=$ (CH$_3$)$_2$CH— and $R_3=$CH$_3$—)

0.65 g (1.44 mmoles) of compound 5-A obtained in Referential Example 5-A is dissolved in 15 ml of t-butanol-water (9:1), 50 mg of 5% palladium carbon is added, and the mixture is stirred under a hydrogen stream for 2 hours. After the reaction, the catalyst is removed by filtration and washed, and the filtrate and the washings are concentrated under reduced pressure. The oily residue is dissolved in 30 ml of benzene and the solution is concentrated again under reduced pressure, and this operation is further repeated once more. The resultant oily matter is dissolved in 6 ml of dimethylformamide, 0.25 g (1.72 mmoles) of N,N-dimethylvaline and 0.29 g (1.78 mmoles) of DEPC are added, the mixture is stirred at room temperature until clear solution is obtained, then the solution is cooled with ice, and the solution of 0.17 g (1.68 mmoles) of triethylamine in 1 ml of dimethylformamide is added dropwise over a period of 4 minutes. Stirring is continued at 0° for at least 4 hours and then overnight during which time the temperature is allowed to rise as the ice melts, the resultant clear reaction mixture is diluted with ethyl acetate, and the ethyl acetate solution is thoroughly washed with saturated aqueous sodium bicarbonate and then dried. The solvent is distilled off, and 0.66 g of the remaining pale brown oily matter is purified by silica gel column chromatography (eluent: ethyl acetate-hexane (1:1)) to obtain 0.46 g (71.9%) of the desired compound 6-A as a colorless oily matter. $[\alpha]_D^{27}$–56.5° (c=1.00, MeOH) $^1$H-NMR (CDCl$_3$, δ) 0.8~1.1(12 H, m), 1.15(3 H, d, J=7.0 Hz), 1.45(9 H, s), 2.27(6 H, s), 3.05(3 H, s), 3.38(3 H, s), 3.55~3.85(1 H, m), 4.35~4.65(1 H, m), 4.65~4.95(1 H, m), 0. 88(1 H, br, d)

The following compounds were obtained in the same manner as in Referential Example 6-A.

| Referential Example | Compound | R$_1$ | R$_2$ | R$_3$ | Yield | Melting point | $[\alpha]_D$* | $^1$H-NMR (CDCl$_3$, δ) |
|---|---|---|---|---|---|---|---|---|
| 6-B | 6-B | H | (CH$_3$)$_2$CH— | (CH$_3$)$_2$CH—CH$_2$— | 58.1% | Oil | –52.7° (26°) | 0.7~1.1(12H, m), 1.46(9H, s), 2.28(6H, s), 3.01(3H, s), 3.37 (3H, s), 3.5~3.85(1H, m), 4.45~4.95(3H, m), 7.65(1H, br, d) |
| 6-C | 6-C | CH$_3$ | (CH$_3$)$_2$CH— | CH$_3$CH(C$_2$H$_5$)— | 61.8% | Oil | –42.9° (26°) | 0.75~1.05(12H, m), 1.25 (3H, d, J=7.0Hz), 1.46(9H, s), 2.25(6H, s), 3.01(3H, s), 3.35(3H, s), 3.7~4.05(1H, m), 4.73(1H, dd, J=9.5Hz, 6.6Hz), 7.62(1H, br, d) |
| 6-D | 6-D | (CH$_3$)$_2$CH— | H | CH$_3$CH(C$_2$H$_5$)— | 90.3% | Oil | –14.5° (26°) | 0.7~1.1(12H, m), 1.46(9H, s), 2.30(6H, s), 2.85(3H, s), 3.37(3H, s), 3.8~4.0(1H, m), 4.0~4.2(2H, m), 4.4~4.65 (1H, m), 7.0~7.15(1H, br) |
| 6-E | 6-E | (CH$_3$)$_2$CH— | (CH$_3$)$_2$CH— | CH$_3$CH$_2$CH$_2$— | 70.3% | Oil | –62.8° (28°) | 0.7~1.1(15H, m), 1.45(9H, s), 2.25(6H, s), 3.02(3H, s), 3.37 (3H, s), 3.5~3.85(1H, m), 4.35~4.65(1H, m), 4.74 (1H, dd, J=9.2Hz, 6.4Hz), 6.84(1H, br, d) |
| 6-F | 6-F | (CH$_3$)$_2$CH— | (CH$_3$)$_2$CH— | (CH$_3$)$_2$CH— | 77.5% | 122° | –51.0° (27°) | 0.7~1.15(18H, m), 1.46(9H, s), 2.25(6H, s), 3.02(3H, s), 3.35(3H, s), 3.7~4.0(1H, m), 4.3~4.6(1H, m), 4.65~4.9 (1H, m), 6.86(1H, br, d) |
| 6-G | 6-G | (CH$_3$)$_2$CH— | (CH$_3$)$_2$CH— | (CH$_3$)$_2$CH—CH$_2$— | 79.2% | Oil | –57.8° (26°) | 0.7~1.1(18H, m), 1.46(9H, s), 2.25(6H, s), 3.01(3H, s), 3.36(3H, s), 3.5~3.8(1H, m), 4.80(1H, dd, J=9.2Hz, 6.2Hz), 6.85(1H, br, d) |
| 6-H | 6-H | (CH$_3$)$_2$CH— | (CH$_3$)$_2$CH— | CH$_3$CH(C$_2$H$_5$)— | 84.7% | 112° | –44.4° (27°) | 0.65~1.15(18H, m), 1.46 (9H, s), 2.26(6H, s), 3.01 (3H, s), 3.35(3H, s), 3.7~4.05(1H, m), 4.80 (1H, dd, J=9.2Hz, 6.4Hz), 6.89(1H, br, d) |
| 6-I | 6-I | CH$_3$CH(C$_2$H$_5$)— | (CH$_3$)$_2$CH— | (CH$_3$)$_2$CH—CH$_2$— | 80.1% | Oil | –59.2° (26°) | 0.7~1.1(18H, m), 1.46(9H, s), 2.24(6H, s), 3.01(3H, s), 3.36(3H, s), 3.5~3.85(1H, m), 4.5~4.95(2H, m), 6.95 (1H, br, d) |
| 6-J | 6-J | CH$_3$CH(C$_2$H$_5$)— | CH$_3$CH(C$_2$H$_5$)— | CH$_3$CH(C$_2$H$_5$)— | 68.6% | 93° | –43.3° (27°) | 0.7~1.1(18H, m), 1.46(9H, s), 2.25(6H, s), 3.01(3H, s), 3.34(3H, s), 3.7~4.0(1H, m), 4.5~4.95(2H, m), 6.90 (1H, br, d) |

| Referential Example | Compound | $R_1$ | $R_2$ | $R_3$ | Yield | Melting point | $[\alpha]_D$* | $^1$H-NMR (CDCl$_3$, δ) |
|---|---|---|---|---|---|---|---|---|
| 6-K | 6-K | H | CH$_3$\\CH—/CH$_3$ | C$_2$H$_5$\\CH—/CH$_3$ | 72.7% | Oil | −25.7°** (24°) | 0.7–1.1(12H, m), 1.46(9H, s), 2.42(6H, s), 3.00(3H, s), 3.35 (3H, s), 3.7–4.0(1H, m), 4.74 (1H, dd, J=9.0Hz, J=6.4Hz), 7.75(1H, br. d) |
| 6-L | 6-L | CH$_3$\\CH—/CH$_3$ | PhCH$_2$— | C$_2$H$_5$\\CH—/CH$_3$ | 86.0% | Oil | −18.0° (27°) | 0.7–1.0(15H, m), 1.48(9H, s), 2.19(6H, s), 2.76(3H, s), 3.31 (3H, s), 3.6–3.9(1H, m), 4.3–4.7(1H, m), 5.26(1H, dd, J=8.8Hz, 7.7Hz), 6.87(1H, br, d), 7.26(5H, s) |
| 6-M | 6-M | CH$_3$\\CH—/CH$_3$ | C$_2$H$_5$\\CH—/CH$_3$ | C$_2$H$_5$\\CH—/CH$_3$ | 72.5% | 104° | −45.7° (27°) | 0.7–1.1(18H, m), 1.46(9H, s), 2.27(6H, s), 3.01(3H, s), 3.34 (3H, s), 3.7–4.0(1H, m), 4.82 (1H, dd, J=9.2Hz, J=7.0Hz), 6.80(1H, br, d) |

*c = 1.00, MeOH
**CHCl$_3$ (c = 0.315)

REFERENTIAL EXAMPLE 7

Preparation of compound 7-A (Compound 7 wherein $R_4$=H)

7 ml (15.5 mmoles) of a 23.86 LDA tetrahydrofuran: hexane (1:1) solution is added dropwise to 10 ml of anhydrous tetrahydrofuran at −20° C. under a nitrogen atmosphere and stirring. Then the mixture is cooled to −78° C. in a dry ice-acetone bath. 2.3 g (15 mmoles) of benzyl acetate is added dropwise over a period of 30 minutes, the mixture is stirred at −78° C. for 5 minutes, and a solution of 2.0 g (10 mmoles) of BoC-L-prolinal in 10 ml of tetrahydrofuran is added dropwise over a period of 1 hour. The mixture is stirred at −78° C. for 10 minutes, 30 ml of ice-cooled 1N hydrochloric acid is added, and the temperature is elevated up to room temperature. The mixture is extracted with ethyl acetate, the extract is washed with water and dried, the solvent is distilled off under reduced pressure, and the residue is purified by silica gel flash chromatography using hexane: ethyl acetate (5:1) as an eluent to obtain 1.12 g (32.0) of the desired compound 7-A as an oily matter. $[\alpha]_D^{25}$−23.7° (c=1.26, CHCl$_3$) MS 331, 276 $^1$H-NMR (CDCl$_3$, δ) 1.46(9 H, s), 2.47(2 H, d, J=6.8 Hz), 3.7–4.3(2 H, m), 5.15(2 H, s), 7.2–7.4(5 H, m)

REFERENTIAL EXAMPLE 8

Preparation of compound 8-A (Compound 8 wherein $R_4$=H)

560 mg (1.6 mmoles) of compound 7-A obtained in Referential Example 7 is dissolved in 27 ml of dichloromethane, 202 μl (1.6 mmoles) of BF$_3$.Et$_2$O is added thereto under cooling in ice-salt bath, and an ether solution of diazomethane (32 mmoles) is added dropwise over a period of 30 minutes. After stirring for further two hours under cooling in ice-salt bath, 2 ml of saturated aqueous sodium bicarbonate is added. The insoluble matter is removed by filtration, the filtrate is extracted with ethyl acetate, and the extract is washed with water and dried. The solvent is distilled off under reduced pressure, and the residue is purified by silica gel flash chromatography using hexane: ethyl acetate (5:1) as an eluent to obtain 378 mg (65.0%) of the desired compound 8-A as an oily matter. $[\alpha]_D^{25}$−58.7° (c=0.52, CHCl$_3$) MS 241, 218 $^1$H-NMR (CDCl$_3$, δ) 1.46(9 H, s), 2.47(2 H, d, J=7.5 Hz), 3.34(3 H, s) 3.6–4.3(2 H, m), 5.14(2 H, s), 7.2–7.4(5 H, m)

REFERENTIAL EXAMPLE 9

Preparation of compound 9-A (Compound 9 wherein $R_5$=CH$_3$)

6.82 g (60 mmoles) of cysteamine hydrochloride is dissolved in 50 ml of dimethylformamide, and the solution is neutralized with 8.4 ml of triethylamine. The solution is mixed with a solution of crude Boc-L-alaninal obtained by oxidizing 8.75 g (50 mmoles) of Boc-alaninol in 50 ml of dimethylformamide, and mixture is stirred overnight at room temperature. The solvent is distilled off under reduced pressure, the formed crystals are dissolved in ethyl acetate, the solution is washed with 10% citric acid and saturated aqueous sodium bicarbonate, and the ethyl acetate layer is dried. The solvent is distilled off under reduced pressure to obtain 4.93 g (42.6%) of the desired compound 9-A as white crystals. Melting point 81.0°–84.1° C. MS 232 (M$^+$), 159 $^1$H-NMR (CDCl$_3$, δ) 1.24(3 H, d, J=6.6 Hz), 1.45(9 H, s), 2.1(1 H, br), 4.42(1 H, d, J=8.1 Hz)

REFERENTIAL EXAMPLE 10

Preparation of compound 10-A (Compound 10 wherein $R_3$=CH$_3$)

1 34 g (5.77 mmoles) of the compound 9-A obtained in Referential Example 9 and 12.5 g of manganese dioxide are stirred in 58 ml of benzene at 55° C. for 1.5 hours. The suspension is filtered, the solvent is distilled off under reduced pressure, and the residue is purified by silica gel flash chromatography using hexane: ethyl acetate (5:1) as an eluent to obtain 118 mg (9.0%) of the desired compound 10-A as an oil matter. $[\alpha]_D^{22}$−36.0° (c=1.29, CH$_2$Cl$_2$) MS228(M$^+$) 172 $^1$H-NMR (CD$_2$Cl$_2$, δ) 1.43(9 H, s), 1.56(3 H, d, J=7.2 Hz), 4.9–5.2(2 H, m), 7.26(1 H, d, J=3.3 Hz), 7.67 (1 H, d, J=3.3 Hz).

REFERENTIAL EXAMPLE 11-A

Preparation of compound 11-A (Compound 11 wherein $R_4$=H and $R_5$=PhCH$_2$)

220 mg (0.604 mmole) of compound 8-A obtained in Referential Example 8 is dissolved in 9 ml of t-butanol: water (9:1), 50 mg of palladium carbon is added and the mixture is stirred under a hydrogen stream. After completion of the reaction, the reaction solution is filtered, and the solvent is distilled off under reduced pressure to obtain 165 mg (0.604 mmole) of a solid matter. This is dissolved in 3 ml of acetonitrile, 267 mg (0.604 mmole) of the BOP reagent and 192 mg (0.604 mmole) of a trifluoroacetate salt obtained from known compound 10-B (compound 10 wherein $R_5$=$CH_2$Ph) are added, and then 195 mg (1.51 mmoles) of diisopropylethylamine is added dropwise under ice cooling. The mixture is stirred overnight at room temperature, the solvent is distilled off under reduced pressure, the residue is dissolved in dichloromethane, and the solution is washed successively with 10% citric acid, saturated aqueous sodium bicarbonate and saturated saline and dried. The solvent is distilled off under reduced pressure, and the resultant crude product is purified by silica gel column chromatography using dichloromethane-methanol (50:1)) as an eluent to obtain 262 mg (94.4%) of the desired compound 11-A as amorphous powder. $[\alpha]_D^{27}$ −86.4° (c=0.43, MeOH) MS 428, 368 $^1$H-NMR (CDCl$_3$, δ) 1.47(9 H, s), 2.29(2 H, d, J=6.2 Hz), 3.27(3 H, s), 5.63(1 H, m), 7.1~7.3(6 H, m), 7.40(1 H, d, J=3.3 Hz)

REFERENTIAL EXAMPLE 11-B

Preparation of compound 11-B (Compound 11 wherein $R_4$=$CH_3$ and $R_5$=$CH_3$)

Compound 8-B (compound 8 wherein $R_4$=$CH_3$), known compound, and compound 10-A obtained in Referential Example 10 are treated in all the same manner as in Referential Example 11-A to obtain the desired compound 11-B. Yield 62.0%, an oily matter. $[\alpha]_D^{26}$ −100° (c=1.3, MeOH) MS 365, 324, 309 $^1$H-NMR (CDCl$_3$, δ) 1.26(3 H, d, J=6.7 Hz), 1.48(9 H, s), 1.63(3 H, d, J=6.7 Hz), 3.43(3 H, s), 5.2~5.6(1 H, m), 7.23(1 H, d, J=3.3 Hz), 7.69(1 H, s, J=3.3 Hz)

REFERENTIAL EXAMPLE 12-A

Preparation of compound 13-C (Compound 13 wherein $R_6$=$OCH_2$Ph)

solvents are distilled off under reduced pressure, and the resultant crude product is purified by preparative TLC (developing solvent, hexane: ethyl acetate =2:1) to obtain 79.6 mg (91.0%) of crystals (compound 13-C) having a melting point of 111.5° to 113.4°. $[\alpha]_D^{26}$ +8.38° (c=0.37, MeOH) MS 438(M$^+$), 382, 365 $^1$H-NMR (CDCl$_3$, δ) 1.38(9 H, s), 3.31(2 H, br. d, J=5.5 Hz), 5.1~5.3(2 H, m), 5.4(2 H, s), 7.0~7.5(10 H, m), 8.04 (1 H, s)

REFERENTIAL EXAMPLE 12-B

Preparation of compound 13-D (Compound 13 wherein $R_6$=NHPh)

28.2 mg (0.0809 mmole) of compound 13-B is dissolved in 0.5 ml of dichloromethane, 35.8 mg (1.0 equivalent) of the BOP reagent and 9 mg (1.2 equivalents) of aniline are added, and 15.7 mg (1.5 equivalents) of diisopropylethylamine is added dropwise under water cooling. The reaction solution is stirred overnight at room temperature and then concentrated under reduced pressure, The residue is dissolved in dichloromethane, and the solution is washed successively with 10% aqueous citric acid, saturated aqueous sodium bicarbonate and saturated saline, and dried. The crude product is purified by preparative TLC using hexane-ethyl acetate (2:1) as a developing solvent to obtain 35 mg (100%) of the desired compound as crystals. $[\alpha]_D^{26}$ −15.7° (c=0.305, MeOH) MS 423, 363 $^1$H-NMR (CDCl$_3$, δ) 1.42(9 H, s), 3.31(2 H, d J=6.4), 4.9–5.4 (2 H, m), 7.0~7.8(11 H, m), 8.09(1 H, s)

Referential Examples 12-C and 12-D are carried out in the same manner as above to obtain the following compounds.

| Referential Example | Compound | $R_6$ | Yield | $[\alpha]_D$ | MS | $^1$H-NMR (CDCl$_3$, δ) |
|---|---|---|---|---|---|---|
| 12-C | 13-E | —NH-Bu$^t$ | 100% | −21.0° (c = 0.315, CHCl$_3$) (25°) | 404 348 | 1.40(9H, s), 1.49(9H, s), 3.27(2H, d, J=5.9Hz), 5.0–5.4(2H, m), 7.0–7.4 (6H, m), 7.93(1H, s) |
| 12-D | 13-F |  | 96.4% | −28.2° (c = 0.355, CHCl$_3$ (25°) | 417 361 | 1.41(9H, s), 3.25(2H, d, J=6.4Hz), 3.76(8H, br.), 5.0–5.5(2H, m), 6.9–7.3 (6H, m), 7.84(1H, s) |

870 mg (2.4 mmoles) of compound 13-A (compound 13 wherein R=$OCH_3$), known compound, is dissolved in 5 ml of ethanol, and 3 ml of 1N sodium hydroxide is added. The mixture is stirred at room temperature for 30 minutes, the solvent is distilled off under reduced pressure, water is added, the mixture is acidified with citric acid, and the mixture is extracted with ethyl acetate. The extract is washed with water and dried over anhydrous sodium sulfate, and the solvent is distilled off under reduced pressure to obtain 680 mg (83.3%) of crystals of compound 13-B (compound 13 wherein $R_6$=OH).

70 mg (0.2 mmole) of the crystals are dissolved in 0.5 ml of dichloromethane, 2.4 mg (0.02 mmole) of 4-dimethylaminopyridine and 30 mg (2.4 mmoles) of benzyl alcohol are added, and 50 mg (2.4 mmoles) of DCC is added under ice cooling. The mixture is stirred under ice cooling for 1 hour and then overnight at room temperature. The deposited crystals are removed by filtration, and the filtrate is diluted with ethyl acetate, washed with saturated aqueous sodium bicarbonate and saturated saline, and dried. The

REFERENTIAL EXAMPLE 13-A

Preparation of compound 15-A (Compound 15 wherein $R_4$=$CH_3$ and $R_6$=$OCH_3$)

330 mg (0.91 mmole) of compound 13-A, known compound, is dissolved in 1.4 ml of dichloromethane, 0.6 ml of trifluoroacetic acid is added under ice cooling, and the mixture is stirred at room temperature for 1.5 hours. The solvent is distilled off under reduced pressure, and ether is added to cause crystallization. The white crystals are collected by filtration and dried. Yield: 339 mg (98.9%).

314 mg (0.835 mmole) of the crystals are dissolved in 4.2 ml of acetonitrile, 369 mg (0.835 mmole) of the BOP reagent and 240 mg (0.835 mmole) of compound 14 ($R_4$=$CH_3$), known compound, are added, and 270 mg (2.09 mmoles) of diisopropylethylamine is added dropwise under ice cooling. The reaction solution is stirred overnight at room temperature, diluted with ethyl acetate, washed successively with 10% aqueous citric acid, saturated aqueous sodium bicarbonate and saturated saline, and dried. The crude product is purified by silica gel column chromatography using dichloromethane-methanol (50:1) as an eluent to obtain 431 mg (97.1%) of the desired compound 15-A as powder. $[\alpha]^{29}_D$ −61.5° (c=1.02, MeOH) MS 499, 440 $^1$H-NMR (CDCl$_3$, δ) 1.12(3 H, d, J=7.0 Hz), 1.47(9 H, s), 3.35 (3 H, s), 3.95(3 H, s), 5.4–5.7(1 H, m), 7.22(6 H, m), 8.05(1 H, s)

The following compounds were obtained in the same manner as in Referential Example 13-A.

reagent and 14.1 mg (1.1 equivalents) of phenethylamine are added, and 20.6 mg (1.5 equivalents) of diisopropylethylamine is added dropwise under ice cooling. The reaction solution is stirred overnight at room temperature, and concentrated under reduced pressure. The residue is dissolved in dichloromethane, and the solution is washed successively with 10% aqueous citric acid, saturated aqueous sodium bicarbonate and saturated saline, and dried. The crude product is purified by preparative TLC using dichloromethane-

| Referential Example | Compound | R$_4$ | R$_6$ | Yield | $[\alpha]_D$ (MeOH) | MS | $^1$H-NMR (CDCl$_3$, δ) |
|---|---|---|---|---|---|---|---|
| 13-B | 15-B | CH$_3$ | OCH$_2$Ph | 86.8% | −55.8° (c = 1.11) (25°) | 607 575 | 1.21(3H, d, J=7.0Hz), 1.46(9H, s), 3.34(3H, s), 5.40(2H, s), 5.56(1H, m), 7.1–7.5(11H, m), 8.05(1H, m) |
| 13-C | 15-C | H | OCH$_3$ | 83.7% | −67.2° (c = 1.96) (25°) | 518 490 | 1.46(9H, s), 3.27(3H, s), 3.95(3H, s), 5.60(1H, m), 7.0–7.3(6H, m), 8.05(1H, s) |
| 13-D | 15-D | CH$_3$ | NHPh | 99.7% | −38.5° (c = 0.33) (27°) | 593 560 | 1.15(3H, d, J=7.0Hz), 1.48(9H, s), 3.38(3H, s), 7.1–7.8(11H, m), 8.08(1H, s) |
| 13-E | 15-E | CH$_3$ | NH-Bu$^+$ | 96.9% | −62.3° (c = 0.326) (27°) | 572 540 | 1.14(3H, d, J=7.0Hz), 1.48(18H, s), 2.05(2H, br.), 3.36(3H, s), 7.0–7.4(6H, m), 7.92(1H, s) |
| 13-F | 15-F | CH$_3$ | —N⟨O⟩ | 100% | −57.5° (c = 0.323) (26°) | 587 554 | 1.14(3H, d, J=6.8Hz), 1.48(9H, s), 3.36(3H, s), 7.0–7.4(6H, m), 7.82(1H, s) |

REFERENTIAL EXAMPLE 14-A

Preparation of compound 17-A (Compound 17 wherein —A$_2$—R$_7$=CH$_2$CH$_2$—Ph)

30.5 mg (0.106 mmole) of a carboxylic acid obtained from known compound 8-B (compound 8 wherein R$_4$=CH$_3$) according to Referential Example 11 is dissolved in 1 ml of acetonitrile, 51.6 mg (1.1 equivalents) of the BOP methanol (10:1) as a developing solvent to obtain 38.3 mg (92.5%) of the desired compound 17-A as powder. $[\alpha]^{26}_D$ −21.6° (c=1.02, MeOH) MS 358, 317 $^1$H-NMR (CDCl$_3$, δ) 1.19(3 H, d, J=7.0 Hz), 1.48(9 H, s), 3.37 (3 H, s), 7.1–7.4(5 H, m)

The following compounds were obtained in the same manner as in Referential Example 14-A.

| Referential Example | Compound | -A$_2$-R$_7$ | Yield | $[\alpha]_D$ (MeOH) | MS | $^1$H-NMR (CDCl$_3$, δ) |
|---|---|---|---|---|---|---|
| 14-B | 17-B | -Ph | 80.6% | −59.4° (c = 0.204) (29°) | 330 289 | 1.33(3H, d, J=7.0Hz), 1.48(9H, s), 3.51(3H, s), 7.0–7.7(5H, m) |
| 14-C | 17-C | —CH$_2$Ph | 86.6% | −19.2° (c = 0.285) (29°) | 344 303 | 1.26(3H, d, J=7.0Hz), 1.47(9H, s), 3.42(3H, s), 4.43(2H, d, J=5.7Hz), 7.30(5H, s) |
| 14-D | 17-D | —CH$_2$CH$_2$CH$_2$Ph | 87.2% | −36.1° (c = 0.23) (28°) | 372 331 | 1.22(3H, d, J=7.0Hz), 1.47(9H, s), 3.44(3H, s), 7.1–7.4(5H, m) |
| 14-E | 17-E | —CH$_2$—CH(S)(CH$_3$)—Ph | 87.7% | −111.6° (c = 0.865) (25°) | 391 358 | 1.23(3H, d, J=7.0Hz), 1.45(9H, s), 3.40(3H, s), 7.1–7.4(5H, m) |
| 14-F | 17-F | —CH$_2$CH$_2$—⟨H⟩ (cyclohexyl) | 66.8% | −36.5° (c = 1.145) (26°) | 397 364 | 1.23(3H, d, J=6.8Hz), 1.48(9H, s), 3.44(3H, s) |

-continued

| Referential Example | Compound | -A₂-R₇ | Yield | [α]_D (MeOH) | MS | ¹H-NMR (CDCl₃, δ) |
|---|---|---|---|---|---|---|
| 14-G | 17-G | —CH₂CH₂— 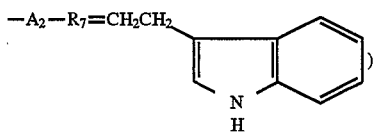 | 91.2% | −27.2° (c=0.328) (29°) | 440 408 | 1.20(3H, d, J=7.0Hz), 1.47(9H, s), 3.37(3H, s), 7.2–8.2(7H, m) |
| 14-H | 17-H | 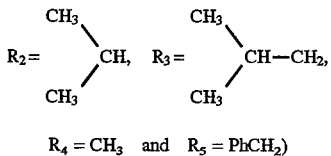 | 71.7% | −73.2° (c=0.342) (29°) | 337 296 | 1.35(3H, d, J=7.0Hz), 1.47(9H, s), 3.51(3H, s), 6.97(1H, d, J=3.7Hz), 7.45(1H, d, J=3.7Hz) |

REFERENTIAL EXAMPLE 15

Preparation of compound 18-A (Compound 18 wherein

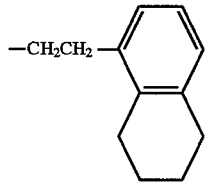

)

Compound 18-A was obtained in the same manner as in Referential Example 14-A from tryptamine and a benzyloxycarbonylated carboxylic acid obtained from compound 8 as a starting material through the steps of debenzylation (see Referential Example 11), de-tert-butoxycarbonylation and benzyloxycarbonylation as shown in Flow sheet 6. $[\alpha]^{28}_D$ −6.4° (c=1.41, MeOH) MS 593, 560 ¹H-NMR (CDCl₃, δ) 1.0–1.3(3 H, m), 3.28(3 H, s), 6.9–8.0(6 H, m)

EXAMPLE 1

Preparation of compound 12-A (Compound 12 wherein $R_1$,

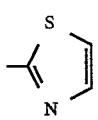

$R_4 = CH_3$ and $R_5 = PhCH_2$)

1 ml of concentrated hydrochloric acid is added with ice cooling to 108 mg (0.222 mmole) of compound 6-G obtained in Referential Example 6-G, and the mixture is stirred for 1 hour. The mixture is evaporated to dryness under reduced pressure, the residue is dissolved in 2 ml of dimethylformamide, and 0.15 ml of triethylamine is added under ice cooling. Although triethylamine hydrochloride is deposited, the mixture is evaporated to dryness under reduced pressure and dried. On the other hand, 105 mg (0.222 mmole) of known compound 11-C (compound 11 wherein $R_4=CH_3$ and $R_5=PhCH_2$) is dissolved in 0.4 ml of ethyl acetate, and 3.3 ml of 2N hydrogen chloride/ethyl acetate is added under ice cooling. The mixture is stirred at room temperature for 1 hour, the solvent is distilled off under reduced pressure, and the residue is dried. The resultant hygroscopic crystals are dissolved in 1.6 ml of dimethylformamide and is added to the above tripeptide carboxylic acid, and 40 mg (0.222 mmole) of 90% DEPC and 62 μl (0.444 mmole) of triethylamine are added under ice cooling. The mixture is stirred for 1 hour under ice cooling and then overnight at room temperature. The solvent is distilled off under reduced pressure, the residue is dissolved in dichloromethane, and the solution is washed with saturated aqueous sodium bicarbonate and saturated saline and dried. The solvent is distilled off, the residue is purified by silica gel flash chromatography using dichloromethane-methanol (20:1) as an eluent, and the fractions containing the desired compound is further purified by Sephadex LH-20 chromatography using hexane: dichloromethane: methanol (2:7.5:2.5) as an eluent to obtain 137 mg (78.4%) the desired compound 12-A as amorphous powder. $[\alpha]_D^{27}$ −89.0° (c=0.60, MeOH) MS 741, 693 ¹H-NMR (CDCl₃, δ) 2.32(6 H, s), 2.96(3 H, s), 3.32(3 H, s), 3.40(3 H, s), 5.56(1 H, m), 6.8–7.3(9 H, m), 7.73(1 H, d, J=3.3 Hz)

EXAMPLES 2–14

The following compounds were obtained by carrying out Examples 2–14 in the same manner as in Example 1.

| Example | Compound | R₁ | R₂ | R₃ | R₄ | R₅ | $[\alpha]_D$ (MeOH) | MS | ¹H-NMR (CD₂Cl₂, δ) |
|---|---|---|---|---|---|---|---|---|---|
| 2 | 12-B | (CH₃)₂CH— | H | CH₃CH(C₂H₅)— (CH₃-CH-, with C₂H₅) | CH₃ | PhCH₂— | −61.6° (25°) c=1.30 | 742(M+) 699 667 | 2.29(6H, s), 2.82 (3H, s), 3.31(3H, s), 3.33(3H, s), 5.52(1H, m), 6.9~7.4(9H, m), 7.73 (1H, d, J=3.3Hz) |
| 3 | 12-C | (CH₃)₂CH— | (CH₃)₂CH— | CH(C₂H₅)(CH₃)— | CH₃ | CH₃ | −84.9° (26°) c=1.02 | 665 | 1.24(3H, d, J=7.0Hz), 1.60(3H, d, J=7.0Hz), 2.23(6H, s), 2.99(3H, s), 3.30(3H, s), 3.39(3H, s), 6.75(1H, d, J=9.2Hz), 7.12(1H, d, J=8.1Hz), 7.25(1H, d, J=3.3Hz), 7.66(1H, d, J=3.3Hz), |
| 4 | 12-D | (CH₃)₂CH— | (CH₃)₂CH— | CH(C₂H₅)(CH₃)— | CH₃ | PhCH₂— | −79.4° (23°) c=0.33 | 770(M+) 727 679 | 2.48(6H, s), 3.02 (3H, s), 3.32(6H, s), 7.0~7.4(9H, s), 7.71(1H, d, J=3.3Hz) |
| 5 | 12-E | (CH₃)₂CH— | (CH₃)₂CH— | CH(C₂H₅)(CH₃)— | H | PhCH₂— | −76.1° (28°) c=0.47 | 770(M+) 727 679 | 2.27(6H, s), 3.02(3H, s), 3.25(3H, s), 3.29(3H, s), 5.62(1H, m), 6.88 (1H, d, J=9.0Hz), 7.1~7.3(6H, m), 7.59 (1H, d, J=7.9Hz), 7.73(1H, d, J=3.3Hz), |
| 6 | 12-F | CH(C₂H₅)(CH₃)— | (CH₃)₂CH— | (CH₃)₂CH—CH₂— | CH₃ | PhCH₂— | −87.5° (24°) c=0.33 | 798(M+) 755 741 | 2.21(6H, s), 2.96(3H, s), 3.32(3H, s), 3.38(3H, s), 5.52(1H, m), 6.85 (1H, d, J=8.8Hz), 7.0~7.3(7H, m), 7.72(1H, d, J=3.3Hz), |
| 7 | 12-G | CH(C₂H₅)(CH₃)— | CH(C₂H₅)(CH₃)— | CH(C₂H₅)(CH₃)— | CH₃ | PhCH₂— | −80.6° (24°) c=0.37 | 812(M+) 755 721 | 2.21(6H, s), 3.01(3H, s), 3.31(6H, s), 5.51(1H, m), 6.79(1H, d, J=9.2Hz), 7.1~7.5(7H, m), 7.71 (1H, d, J=3.3Hz), |
| 8 | 12-H | (CH₃)₂CH— | (CH₃)₂CH— | (CH₃)₂CH—CH₂— | H | PhCH₂— | −90.2° (c=0.34) (27°) | 770 727 | 2.97(3H, s), 3.24 (3H, s), 3.36(3H, s), 5.63(1H, m), 7.1-7.3 (7H, m), 7.73(1H, d, J=3.3Hz) |
| 9 | 12-I | (CH₃)₂CH— | CH(C₂H₅)(CH₃)— | CH(C₂H₅)(CH₃)— | CH₃ | PhCH₂— | −70.4° (c=0.26) (27°) | 798 755 | 3.02(3H, s), 3.33 (6H, s), 5.56(1H, m), 7.1~7.3(7H, m), 7.73 (1H, d, J=3.1Hz) |
| 10 | 12-J | (CH₃)₂CH— | (CH₃)₂CH— | CH₃CH₂CH₂— | CH₃ | PhCH₂— | −82.9° (c=0.21) (26°) | 770 727 | 2.97(3H, s), 3.33 (6H, s), 5.56(1H, m), 7.1~7.3(7H, m), 7.73 (1H, d, J=3.1Hz) |
| 11 | 12-K | (CH₃)₂CH— | (CH₃)₂CH— | CH₃ | CH₃ | PhCH₂— | −79.1° (c=0.665) (25°) | 742 699 | 3.28(3H, s), 3.33(6H, s), 5.56(1H, m), 7.1—7.3(7H, m), 7.73(1H, d, J= 3.3Hz) |
| 12 | 12-L | H | (CH₃)₂CH— | CH(C₂H₅)(CH₃)— | CH₃ | PhCH₂— | −79.3° (c=0.545) (24°) | 742 710 | 2.65(6H, s), 3.01 (3H, s), 3.33(6H, s), 5.55(1H, m), 7.1–7.3(7H, m), 7.73(1H, d, J=3.1Hz) |
| 13 | 12-M | (CH₃)₂CH— | PhCH₂— | CH(C₂H₅)(CH₃)— | CH₃ | PhCH₂— | −67.8° (c=0.905) (25°) | 832 789 | 2.90(3H, s), 3.33 (3H, s), 3.34(3H, s), 5.56(1H, m), 7.1–7.3(7H, m), 7.72(1H, d, J=3.3Hz) |

| Example | Compound | R₁ | R₂ | R₃ | R₄ | R₅ | $[\alpha]_D$ (MeOH) | MS | ¹H-NMR (CD₂Cl₂, δ) |
|---|---|---|---|---|---|---|---|---|---|
| 14 | 12-N | CH₃ | (CH₃)₂CH— | (C₂H₅)(CH₃)CH— | CH₃ | PhCH₂— | −80.6° (c=0.17) (26°) | 756 665 | 2.44(6H, s), 3.02 (3H, s), 3.33(6H, s), 5.40(1H, m), 7.1–7.3(7H, m), 7.73(1H, d, J=3.1Hz) |

EXAMPLE 15

Preparation of compound 16-A (Compound 16 wherein

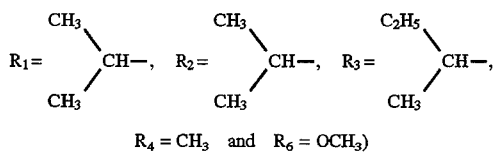

R₄ = CH₃ and R₆ = OCH₃)

0.5 ml of concentrated hydrochloric acid is added to 93 mg (0.192 mmole) of compound 6-H under ice cooling, and the mixture is stirred for 1 hour. The mixture is evaporated to dryness under reduced pressure the residue is dissolved in 2 ml of dimethylformamide, and 0.15 ml of triethylamine is added under ice cooling. Although triethylamine hydrochloride is deposited, the mixture is evaporated to dryness under reduced pressure and dried.

On the other hand, 102 mg (0.192 mmole) of compound 15-A obtained in Referential Example 13-A is dissolved in 0.4 ml of ethyl acetate, and 3.3 ml of 2N hydrogen chloride/ ethyl acetate is added under ice cooling. The mixture is stirred at room temperature for 1 hour, the solvent is distilled off under reduced pressure, and the residue is dried. The resultant hygroscopic crystals are dissolved in 0.8 ml of dimethylformamide, the solution is added to the above tripeptide carboxylic acid, and 35 mg (0.192 mmole) of 90% DEPC and 54 μl (0.384 mmole) of triethylamine are added under ice cooling. The mixture is stirred under ice cooling for 1 hour and then overnight at room temperature.

The solvent is distilled off under reduced pressure, the residue is dissolved in dichloromethane, and the solution is washed with saturated aqueous sodium bicarbonate and saturated saline and dried. The solvent is distilled off, the residue is purified by silica gel flash chromatography using dichloromethane: methanol (30:1) as an eluent, and the fraction containing the desired product are further purified by Sephadex LH-20 chromatography using hexane: dichloromethane: methanol (2:7.5:2.5) as an eluent to obtain 100 mg (62.0%) of the desired compound 16-A as amorphous powder. $[\alpha]^{27}_D$ −64.7° (c=0.66, MeOH) MS 799, 751 ¹H-NMR (CDCl₃, δ) 2.33(6 H, s), 3.02(3 H, s), 3.32(6 H, s), 3.95(3 H, s). 5.53(1 H, m). 6.8–7.5(7 H, m). 8.05(1 H, s)

EXAMPLES 16–22

The following compounds were obtained by carrying out Examples 16 to 22 according to Example 15.

| Example | Compound | R₁ | R₂ | R₃ | R₄ | R₆ | $[\alpha]_D$ (MeOH) | MS | ¹H-NMR (CDCl₃, δ) |
|---|---|---|---|---|---|---|---|---|---|
| 16 | 16-B | (CH₃)₂CH— | (CH₃)₂CH— | (C₂H₅)(CH₃)CH— | CH₃ | OCH₂Ph | −61.6° (c=0.83) (25°) | 886 875 843 | 2.51(6H, br.), 3.02 (3H, s), 3.32(6H, s), 5.39(2H, s), 5.52 (1H, m), 7.0–7.5 (12H, m), 8.04(1H, s) |
| 17 | 16-C | (CH₃)₂CH— | (CH₃)₂CH— | (C₂H₅)(CH₃)CH— | H | OCH₃ | −73.3° (c=0.30) (26°) | 828 785 | 3.02(3H, s), 3.26 (6H, s), 3.95(3H, s), 7.2–7.3(6H, m), 8.05 (1H, s) |
| 18 | 16-D | (CH₃)₂CH— | (CH₃)₂CH— | (CH₃)₂CH—CH₂— | CH₃ | OCH₃ | −71.0° (c=0.465) (26°) | 842 799 | 2.32(6H, s), 2.97 3H, s), 3.32(3H, s), 3.40(3H, s), 3.95 3H, s), 7.2–7.3 (6H, m), 8.05(1H, s) |
| 19 | 16-E | (CH₃)₂CH— | (CH₃)₂CH— | (CH₃)₂CH—CH₂— | H | OCH₃ | −76.8° (c=0.50) (27°) | 828 785 | 2.98(3H, s), 324 (3H, s), 3.34(3H, s), 3.95(3H, s), 5.60(1H, m), 7.1–7.3(6H, m), 8.05 (1H, s) |

-continued

| Example | Compound | R₁ | R₂ | R₃ | R₄ | R₆ | $[\alpha]_D$ (MeOH) | MS | ¹H-NMR (CDCl₃, δ) |
|---|---|---|---|---|---|---|---|---|---|
| 20 | 16-F | $CH_3$<br>$\phantom{xx}$CH—<br>$CH_3$ | $CH_3$<br>$\phantom{xx}$CH—<br>$CH_3$ | $C_2H_5$<br>$\phantom{xx}$CH—<br>$CH_3$ | $CH_3$ | —NHPh | −42.9°<br>(c = 0.385)<br>(27°) | 903<br>860 | 3.00(3H, s), 3.33 (3H, s), 3.34(3H, s), 5.55(1H, m), 5.55 (1H, m), 7.1–7.8 (11H, m), 8.07(1H, s) |
| 21 | 16-G | $CH_3$<br>$\phantom{xx}$CH—<br>$CH_3$ | $CH_3$<br>$\phantom{xx}$CH—<br>$CH_3$ | $C_2H_5$<br>$\phantom{xx}$CH—<br>$CH_3$ | $CH_3$ | —NHBuᵗ | −60.7°<br>(c = 0.29)<br>(28°) | 883<br>868 | 1.48(9H, s), 2.51 (6H, br.), 3.03(3H, s), 3.33(6H, s), 5.49(1H, m), 7.1– 7.3(6H, m), 7.90 (1H, s) |
| 22 | 16-H | $CH_3$<br>$\phantom{xx}$CH—<br>$CH_3$ | $CH_3$<br>$\phantom{xx}$CH—<br>$CH_3$ | $C_2H_5$<br>$\phantom{xx}$CH—<br>$CH_3$ | $CH_3$ | —N⟨morpholino⟩O | −64.4°<br>(c = 0.341) | 897<br>854 | 2.44(6H, br.), 3.03, (3H, s), 3.33(6H, s), 5.56(1H, m), 7.1– 7.3(6H, m), 7.82 (1H, s) |

EXAMPLE 23

Preparation of compound 16-I (Compound 16 wherein

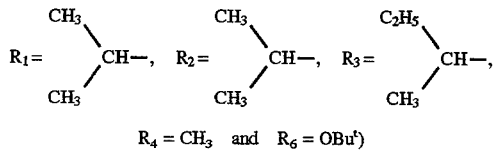

$R_4 = CH_3$ and $R_6 = OBu^t$)

1. 120 mg (0.142 mmole) of compound 16-A is dissolved in 5 ml of dimethylformamide, and 0.16 ml of 1N sodium hydroxide is added under ice cooling. The mixture is stirred under ice cooling for 30 minutes and then at room temperature for 90 minutes. 0.16 ml of 1N hydrochloric acid is added under ice cooling, the solvent is distilled off under reduced pressure, the residue is dissolved in dichloromethane, and the deposited sodium chloride is removed by filtration. The filtrate is purified by Sephadex LH-20 chromatography using hexane dichloromethane: methanol (2:7.5:2.5) as an eluent. The desired product is dissolved again in water, and the solution is lyophilized to obtain 114 mg (96.5%) of compound 16 carboxylic acid ($R_6$=OH) as powder. 2. 30 mg (0.024 mmole) of the above carboxylic acid is dissolved in 0.5 ml of dichloromethane, 10 μl of concentrated sulfuric acid and 1 ml of isobutene are added under cooling in dry ice-acetone bath, and the mixture is stirred for 2 days in a sealed tube. 5 ml of saturated aqueous sodium bicarbonate is added to the reaction solution, the mixture is extracted with dichloromethane, and the extract is washed with water and dried. The solvent is distilled off under reduced pressure, and the residue is purified by Sephadex LH-20 chromatography using hexane: dichloromethane: methanol (2:7.5:2.5) as an eluent to obtain 13 mg (62.5%) of the desired product compound 16-I as amorphous powder. $[\alpha]^{25}_D$−60.6° (c=0.35, MeOH) MS 841, 840, 793 ¹H-NMR (CD₂Cl₂, δ) 1.58(9 H, s), 2.57(6 H, br.), 3.02(3 H, s), 3.31(6 H, s), 5.46(1 H, m), 7.0–7.4(7 H, m), 7.93(1 H, s)

EXAMPLE 24

Preparation of compound 16-J (Compound 16 wherein

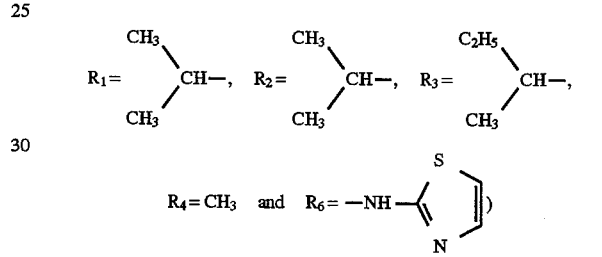

21.5 mg (0.026 mmole) of compound 16 carboxylic acid ($R_6$=OH) is dissolved in 0.5 ml of acetonitrile, 11.5 mg (1 equivalent) of the BOP reagent and 2.6 mg (1 equivalent) of 2-aminothiazole and added, and 5 mg (1.5 equivalents) of diisopropylethylamine is added dropwise under ice cooling. The mixture is stirred overnight at room temperature, and the reaction solution is concentrated under reduced pressure. The concentrate is dissolved in dichloromethane, and the solution is washed successively with 10% aqueous citric acid, saturated aqueous sodium bicarbonate and saturated saline and dried. The crude product is subjected to preparative TLC using dichloromethane-methanol (10:1) as a developing solvent, and are further purified by Sephadex LH-20 chromatography using hexane: dichloromethane: methanol (2:7.5:2.5) as an eluent to obtain 13.7 mg (57.7%) of the desired compound 16-J as amorphous powder. $[\alpha]^{28}_D$ −48.8° (c=0.25, MeOH) MS 910, 867 ¹H-NMR (CDCl₃, δ) 3.01(3 H, s), 3.33(3 H, s), 3.37(3 H, s), 5.52(1 H, m), 7.05(1 H, d, J=3.5 Hz), 7.2–7.3 (6 H, m), 7.50(1 H, d, J=3.3 Hz), 8.16(1 H, s)

EXAMPLE 25

Preparation of compound 16-K (Compound 16 wherein

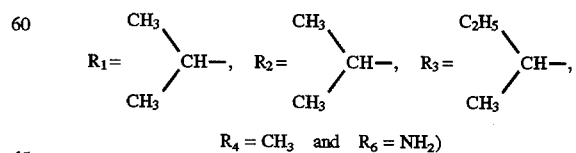

$R_4 = CH_3$ and $R_6 = NH_2$)

21 mg (0.025 mmole) of compound 16-A is dissolved in 3 ml of ammonia-saturated methanol, and the solution is allowed to stand at room temperature for 1 hour. The solvent is distilled off under reduced pressure, and the residue is purified by Sephadex LH-20 using hexane: dichloromethane: methanol (2:7.5:2.5) as an eluent to obtain 20 mg (96.0%) of the desired compound 16-K as amorphous powder. $[\alpha]^{25}_D$ 65.8° (c=0.41, MeOH) MS 784, 736 $^1$H-NMR (CDCl$_3$, δ) 2.48(6 H, s), 3.06(3 H, s), 3.33(6 H, s), 5.50(1 H, m), 7.0–7.6(7 H, m), 8.04(1 H, s)

EXAMPLES 26 AND 27

Compounds shown in the following table were obtained in the same manner as in Example 25 except that 70% aqueous ethylamine solution or 5% aqueous dimethyl-amine solution was used in place of ammonia-saturated methanol.

reduced pressure. On the other hand, 22.3 mg (0.057 mmole) of compound 7-A is dissolved in 2N hydrogen chloride/ethyl acetate under ice cooling, and the mixture is stirred at room temperature for 1 hour. The solvent is distilled off under reduced pressure, the residue is dried and dissolved in 0.5 ml of dimethylformamide, the solution is added to the above tripeptide carboxylic acid, and 9.8 mg (1.0 equivalent) of 95% DEPC and 16 μl (2 equivalents) of triethylamine are added under ice cooling. The mixture is stirred under ice cooling for 1 hour and then overnight at room temperature.

The solvent is distilled off under reduced pressure, and the residue is dissolved in dichloromethane, washed succissively with saturated aqueous sodium bicarbonate and saturated saline, and then dried. The solvent is distilled off, the

| Example | Compound | R$_1$ | R$_2$ | R$_3$ | R$_4$ | R$_6$ | $[\alpha]_D$ (MeOH) | MS | $^1$H-NMR (CDCl$_3$, δ) |
|---|---|---|---|---|---|---|---|---|---|
| 26 | 16-L | (CH$_3$)$_2$CH— | (CH$_3$)$_2$CH— | (C$_2$H$_5$)(CH$_3$)CH— | CH$_3$ | —NHC$_2$H$_5$ | −63.5° (c = 0.32) (25°) | 812 764 | 2.48(6H, s), 3.02 (3H, s), 3.32(6H, s), 5.46(1H, m), 7.0–7.5(7H, m), 7.92 (1H, s) |
| 27 | 16-M | (CH$_3$)$_2$CH— | (CH$_3$)$_2$CH— | (C$_2$H$_5$)(CH$_3$)CH— | CH$_3$ | —N(CH$_3$)$_2$ | −67.1° (c = 0.255) (28°) | 885 812 | 1.67(6H, s), 3.16 (3H, s), 3.33(3H, s), 7.1–7.3(6H, m), 7.26(1H, s) |

EXAMPLE 28

Preparation of compound 19-A (Compound 19 wherein

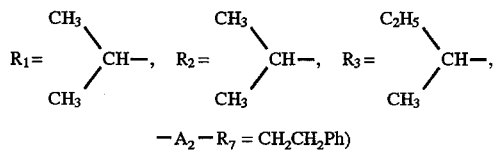

—A$_2$—R$_7$ = CH$_2$CH$_2$Ph)

27.7 mg (0.057 mmole) of compound 6-H is dissolved in 0.3 ml of dichloromethane, and 0.3 ml of trifluoroacetic acid is added under ice cooling. The mixture is stirred at room temperature for 1 hour, the solvent is distilled off under reduced pressure, and the residue is sufficiently dried under residue is subjected to preparative TLC using dichlorometane-methanol (10:1) as a developing solvent, and the fractions of the desired product are further purified by Sephadex LH-20 chromatography using hexane: dichloromethane: methanol (2:7.5:2.5) as an eluent to obtain 35.8 mg (89.5%) of the desired compound 19-A as amorphous powder. $[\alpha]^{25}_D$ −38.0° (c=0.566, MeOH) MS 701, 658 $^1$H-NMR (CD$_2$Cl$_2$, δ) 1.16(3 H, d, J=7.0 Hz), 2.23(6 H, s), 3.00 (3 H, s), 3.30(3 H, s), 3.34(3 H, s)

The following compounds were obtained in the same manner as in Example 28.

| Example | Compound | R$_1$ | R$_2$ | R$_3$ | -A$_2$R$_7$ | $[\alpha]_D$ (MeOH) | MS | $^1$H-NMR (CDCl$_3$, δ) |
|---|---|---|---|---|---|---|---|---|
| 29 | 19-B | (CH$_3$)$_2$CH— | (CH$_3$)$_2$CH— | (C$_2$H$_5$)(CH$_3$)CH— | -Ph | −52.6° (c = 0.352) (28°) | 673 630 | 1.36(3H, d, J=7.0Hz), 3.02(3H, s), 3.34 (3H, s), 3.47(3H, s), 7.0—7.7(6H, m) |
| 30 | 19-C | (CH$_3$)$_2$CH— | (CH$_3$)$_2$CH— | (C$_2$H$_5$)(CH$_3$)CH— | —CH$_2$Ph | −35.8° (c = 0.330) (28°) | 688 644 | 1.28(3H, d, J=7.0Hz), 2.33(6H, br.), 3.01 (3H, s), 3.30(3H, s), 3.39(3H, s), 7.2–7.4(5H, m) |
| 31 | 19-D | (CH$_3$)$_2$CH— | (CH$_3$)$_2$CH— | (C$_2$H$_5$)(CH$_3$)CH— | —CH$_2$CH$_2$CH$_2$Ph | −47.1° (c = 0.312) (27°) | 716 672 | 1.28(3H, d, J=7.0Hz), 2.36(6H, s), 3.00 (3H, s), 3.33(3H, s), 3.41(3H, s), 7.1–7.3(5H, m) |

-continued

| Example | Compound | R₁ | R₂ | R₃ | -A₂R₇ | $[\alpha]_D$ (MeOH) | MS | ¹H-NMR (CDCl₃, δ) |
|---|---|---|---|---|---|---|---|---|
| 32 | 19-E | (CH₃)₂CH– | (CH₃)₂CH– | C₂H₅(CH₃)CH– | –CH₂–CH(S)(CH₃)Ph | –94.8° (c=0.335) (28°) | 658 | 1.49(3H, d, J=7.0Hz), 2.44(6H, br.), 3.02 (3H, s), 3.33(3H, s), 3.38(3H, s), 7.2–7.4(5H, m) |
| 33 | 19-F | (CH₃)₂CH– | (CH₃)₂CH– | C₂H₅(CH₃)CH– | –CH₂CH₂–(cyclohexyl, H) | –48.3° (c=0.265) (28°) | 644 | 2.48(6H, br.), 3.02 (3H, s), 3.33(3H, s), 3.41(3H, s) |
| 34 | 19-G | (CH₃)₂CH– | (CH₃)₂CH– | C₂H₅(CH₃)CH– | –CH₂CH₂–(naphthyl) | –34.1° (c=0.347) (29°) | 708 | 3.00(3H, s), 3.29 (3H, s), 3.34(3H, s), 7.2—8.3(7H, m) |
| 35 | 19-H | (CH₃)₂CH– | (CH₃)₂CH– | C₂H₅(CH₃)CH– | thiazolyl | –61.9° (c=0.315) (29°) | 680 637 | 1.40(3H, d, J=7.0Hz), 2.51(6H, s), 3.15(3H, s), 3.37(3H, s), 3.42 (3H, s), 6.93(1H, d, J=3.5Hz), 7.48(1H, d, J=3.7Hz) |
| 36 | 19-I | H | (CH₃)₂CH– | (CH₃)₂CHCH₂– | –CH₂CH₂Ph | –54.7° (c=0.625) (29°) | 659 644 627 | 1.21(3H, d, J=7.0Hz), 2.42(6H, s), 2.98 (3H, s), 3.35(6H, s), 7.1–7.4(5H, m) |
| 37 | 19-J | (CH₃)₂CH– | (CH₃)₂CH– | (CH₃)₂CHCH₂– | –CH₂CH₂Ph | –53.3° (c=0.368) (28°) | 701 658 | 1.21(3H, d, J=7.3Hz), 2.44(6H, s), 2.98 (3H, s), 3.35(6H, s), 3.38(3H, s), 7.1–7.3, (5H, m) |
| 38 | 19-K | (CH₃)₂CH– | PhCH₂– | C₂H₅(CH₃)CH– | –CH₂CH₂Ph | –18.7° (c=0.307) (30°) | 749 706 | 2.92(3H, s), 3.31 (3H, s), 3.36(3H, s), 7.1–7.4(10H, m) |

EXAMPLE 39

Preparation of compound 19-L (Compound 19 wherein

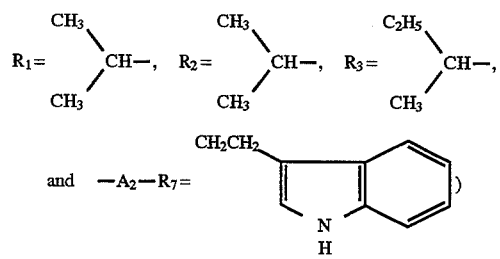

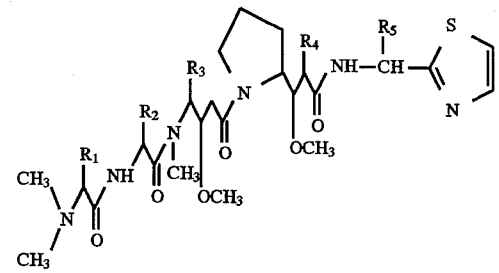

The desired compound 19-L is obtained by reacting a product obtained by removing of Z of compound 18-A according to Referential Example 5-A with compound 6-H according to Example 28. $[\alpha]^{27}_D$ –25.9° (c=0.255, MeOH) MS 740, 697 ¹H-NMR (CDCl₃, δ) 2.64(6 H, br.), 3.03(3 H, s), 3.30(6 H, s), 7.0–7.7(5 H, m), 8.4(1 H, m)

We claim:

1. A tetrapeptide derivative having the following formula or a salt thereof wherein, both R₁ and R₂ represent isopropyl groups, R₃ represents an isobutyl group, an isopropyl group or a n-propyl group, R₄ represents a methyl group and R₅ represents a benzyl group.

2. A tetrapeptide derivative having the following formula or a salt thereof

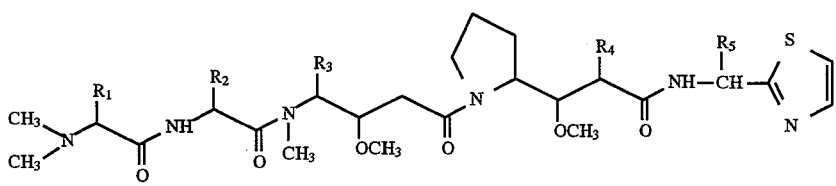

wherein,
both $R_1$ and $R_2$ represent isopropyl groups,
$R_3$ represents a sec-butyl group,
$R_4$ represents a hydrogen atom, and
$R_5$ represents a benzyl group.

3. A tetrapeptide derivative having the following formula or a salt thereof

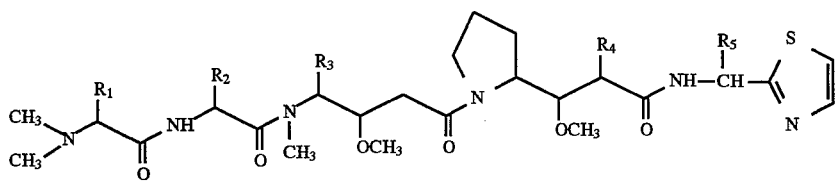

wherein,
$R_1$ represents a hydrogen atom or a methyl group,
$R_2$ represents an isopropyl group,
$R_3$ represents a sec-butyl group,
$R_4$ represents a methyl group, and
$R_5$ represents a benzyl group.

4. A tetrapeptide derivative having the following formula or a salt thereof

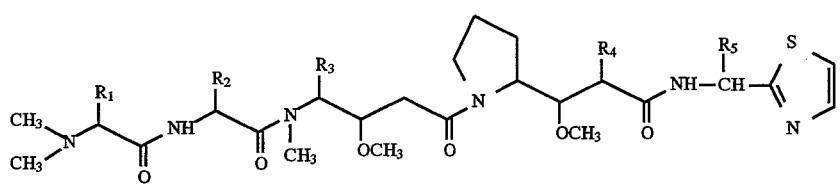

wherein,
$R_1$ represents an isopropyl group,
$R_2$ represents a sec-butyl group or a benzyl group,
$R_3$ represents a sec-butyl group,
$R_4$ represents a methyl group, and
$R_5$ represents a benzyl group.

* * * * *